United States Patent
Shamshiev et al.

(10) Patent No.: US 10,233,238 B2
(45) Date of Patent: Mar. 19, 2019

(54) TNF ALPHA ANTIBODY OR FRAGMENT THEREOF AND METHODS OF USE

(71) Applicant: CELL MEDICA SWITZERLAND AG, Schlieren (CH)

(72) Inventors: Abdijapar Shamshiev, Zurich (CH); Titus Kretzschmar, Steinhausen (CH)

(73) Assignee: Cell Medica Switzerland AG, Schlieren (CH)

( * ) Notice: Subject to any disclaimer, the term of this patent is extended or adjusted under 35 U.S.C. 154(b) by 0 days.

(21) Appl. No.: 15/127,976

(22) PCT Filed: Mar. 26, 2015

(86) PCT No.: PCT/EP2015/056646
§ 371 (c)(1),
(2) Date: Sep. 21, 2016

(87) PCT Pub. No.: WO2015/144852
PCT Pub. Date: Oct. 1, 2015

(65) Prior Publication Data
US 2017/0107282 A1 Apr. 20, 2017

(30) Foreign Application Priority Data

Mar. 26, 2014 (EP) .................................... 14001123

(51) Int. Cl.
*C07K 16/24* (2006.01)
*C12N 15/09* (2006.01)
(Continued)

(52) U.S. Cl.
CPC ...... *C07K 16/241* (2013.01); *A61K 39/39591* (2013.01); *A61K 2039/505* (2013.01);
(Continued)

(58) Field of Classification Search
None
See application file for complete search history.

(56) References Cited

U.S. PATENT DOCUMENTS

| | | | | |
|---|---|---|---|---|
| 9,683,034 B2* | 6/2017 | Ewert | ................ | C07K 16/241 |
| 2006/0024308 A1* | 2/2006 | Crea | ................... | C07K 16/241 |
| | | | | 424/145.1 |
| 2009/0022659 A1* | 1/2009 | Olson | ................. | A61K 49/001 |
| | | | | 424/1.49 |

FOREIGN PATENT DOCUMENTS

| | | |
|---|---|---|
| JP | 2008545433 | 12/2008 |
| JP | 2011526145 | 10/2011 |

(Continued)

OTHER PUBLICATIONS

Yan et al., Construction of a synthetic phage-displayed nanobody library with CDR3 regionsregions randomized by trinucleotide cassettes with diagnostic applications, J. Transl. Med. 12:343, 2014, <https://translational-medicine.biomedcentral.com/articles/10.1186/s12967-014-0343-6> (Year: 2014).*

MacCallum et al., Antibody-antigen interactions:contact analysis and binding site topography, J. Mol. Biol. 262:732-745, 1996. (Year: 1996) (Year: 1996).*

(Continued)

*Primary Examiner* — Claire Kaufman
(74) *Attorney, Agent, or Firm* — Myers Bigel, P.A.

(57) ABSTRACT

The present invention relates to anti-TNF alpha binding members and in particular to monovalent, high potency TNF alpha-binding antibody fragments being highly stable and soluble. Such binding members may be used in the treatment of inflammatory and other diseases as well as in diagnostics. Also provided are related nucleic acids, vectors, cells, and compositions.

24 Claims, 3 Drawing Sheets

Specification includes a Sequence Listing.

(51) Int. Cl.
*G01N 33/53* (2006.01)
*A61K 39/395* (2006.01)
*A61K 39/00* (2006.01)

(52) U.S. Cl.
CPC ...... *C07K 2317/24* (2013.01); *C07K 2317/33* (2013.01); *C07K 2317/565* (2013.01); *C07K 2317/622* (2013.01); *C07K 2317/76* (2013.01); *C07K 2317/92* (2013.01); *C07K 2317/94* (2013.01)

(56) References Cited

FOREIGN PATENT DOCUMENTS

| JP | 2012524071 | 10/2012 |
|---|---|---|
| RU | 2401843 C2 | 10/2010 |
| WO | 2006/014477 | 2/2006 |
| WO | 2006/131013 | 12/2006 |
| WO | 2007/114826 A1 | 10/2007 |
| WO | 2008/144753 | 11/2008 |
| WO | 2010/006454 | 1/2010 |
| WO | 2010/121140 | 10/2010 |
| WO | 2011/084714 | 7/2011 |

OTHER PUBLICATIONS

Lamminmaki et al., Chrystal structure of a recombinant anti-estradiol Fab fragment in complex with the 17beta-estradiol, J. Blol. Chem. 276:36687-94, 2001. (Year: 2001).*
Chen et al., Enhancement and destruction of antibody function by somatic mutation: unequal occurrence is controlled by V gene combinatorial association, EMBO J. 14(12):2784-2794, 1995. (Year: 1995).*
McKay Brown et al., "Tolerance to Single, but not Multiple, Amino Acid Replacements in Antibody V-H CDR2: A Means of Minimizing B Cell Wastage from Somatic Hypermutation?", The Journal of Immunology, The American Association of Immunologists, US, vol. 156, No. 9, Jan. 1, 1996, pp. 3285-3291, XP002649029, ISSN: 0022-1767.
Examination Report corresponding to European Application No. 15712626.9 dated Feb. 1, 2018.
Notification Concerning Transmittal of International Preliminary Report on Patentability corresponding to International Application No. PCT/EP2015/056646 dated Oct. 6, 2018.
Office Action corresponding to Russian Application No. 2016141561 dated Aug. 22, 2018.
Examination Report corresponding to European Application No. 15712626.9 dated Sep. 10, 2018.

* cited by examiner ously active forms: a transmembrane and a soluble form. The soluble form of TNF alpha is released from the transmembrane TNF alpha (tmTNF alpha) by proteolytic cleavage. Both TNF alpha forms are biologically active trimers, bind TNF receptors and exert various biological functions to contribute to the host defence. In addition, both the transmembrane and the soluble TNF alpha play a role in the pathogenesis of inflammatory and autoimmune diseases.

TNF ALPHA ANTIBODY OR FRAGMENT THEREOF AND METHODS OF USE

CROSS-REFERENCE TO RELATED APPLICATIONS

The present application is a 35 § 371 national phase application of PCT/EP2015/056646 filed Mar. 26, 2015 and claims the benefit of and the priority to European patent application EP 14 001 123 filed on 26 Mar. 2014 with the European Patent Office. The content of each of the applications is incorporated herein by reference for all purposes in its entirety including all tables, figures, and claims—as well as including an incorporation of any element or part of the description, claims or drawings not contained herein and referred to in Rule 20.5(a) of the PCT, pursuant to Rule 4.18 of the PCT.

REFERENCE TO A SEQUENCE LISTING

A Sequence Listing in ASCII text format, submitted under 37 C.F.R § 1.821, entitled 1380-3_ST25.txt. 8,396 bytes in size, generated on Sep. 20, 2016 and filed via EFS-Web, is provided in lieu of a paper copy. The Sequence Listing is incorporated herein by reference into the specification for its disclosures.

FIELD OF THE INVENTION

Provided is a binding member against TNF alpha, such as a humanized binding molecule, in particular a monovalent, highly potent and stable anti-TNF alpha reagent, such as an antibody fragment, applicable for therapeutic and diagnostic uses. The binding member is in some embodiments an immunoglobulin, a fragment thereof, or a proteinaceous binding molecule with immunoglobulin-like functions, specific for TNF alpha. Provided is also a nucleic acid molecule encoding such a binding member, a vector containing the sequence of a respective nucleic acid molecule, a host cell containing the vector or the nucleic acid sequence of a respective nucleic acid molecule, a pharmaceutical and a diagnostic composition containing the binding member or the nucleic acid molecule, as well as a use thereof.

BACKGROUND

The following discussion of the background of the invention is merely provided to aid the reader in understanding the invention and is not admitted to describe or constitute prior art to the present invention.

Tumor necrosis factor (TNF) alpha is a potent pro-inflammatory cytokine which plays a central role in immune responses and inflammatory disorders. It has been described as key mediator of inflammatory, immunological and pathophysiological reactions. Primarily secreted by monocytes and activated macrophages, TNF alpha is also produced by numerous other cell types, including fibroblasts, neutrophils, eosinophils and epithelial cells.

Also termed cachectin, TNF alpha exists in two biologically active forms: a transmembrane and a soluble form. The soluble form of TNF alpha is released from the transmembrane TNF alpha (tmTNF alpha) by proteolytic cleavage. Both TNF alpha forms are biologically active trimers, bind TNF receptors and exert various biological functions to contribute to the host defence. In addition, both the transmembrane and the soluble TNF alpha play a role in the pathogenesis of inflammatory and autoimmune diseases.

Two receptors for TNF alpha were identified (TNF-R1 and -R2) mediating the pleiotropic TNF alpha effects. Said receptors are expressed on a variety of cells, mainly on monocytes and macrophages. Receptor activation triggers the various biological effects, including pro-inflammatory cytokine production such as IL-1, TNF alpha, IL-6, IL-8; chemokine production; neutrophil activation; increases endothelium layer's permeability; and expression of adhesion molecules. Accordingly, a large number of diseases is associated with up-regulated TNF alpha levels and consequently, TNF alpha inhibitors have found ample use in medical treatment. An important subclass of the ever growing number of TNF alpha inhibitors are biological drugs. A number of biological inhibitors of TNF alpha received regulatory approval and are commercially available. One group of such biological inhibitors are full-length immunoglobulins. For example, infliximab (Remicade®), a chimeric IgG of about 150 kDa, has been approved in the treatment of Crohn's disease, rheumatoid arthritis, psoriatic arthritis, ulcerative colitis, ankylosing spondylitis, psoriasis, and Behçet disease. Adalimumab (Humira®), an IgG1 of about 150 kDa, is approved for rheumatoid arthritis, juvenile rheumatoid arthritis, Crohn's disease, psoriatic arthritis, psoriasis, ankylosing spondylitis, ulcerative colitis and Behçet disease. Finally, golimumab (Simponi®), a human IgG1 of about 150 kDa molecular weight, is approved in rheumatoid arthritis, psoriatic arthritis, ankylosing spondylitis, and ulcerative colitis.

Still, some approved biological TNF alpha inhibitors deviate from the full-length immunoglobulin structure. For example, etanercept (Enbrel®) is a TNF-receptor 2 extracellular domain Fc fusion protein with a molecular weight of 150 kDa which has been approved for the treatment of rheumatoid arthritis, juvenile rheumatoid arthritis, psoriatic arthritis, psoriasis and ankylosing spondylitis. Further, certolizumab pegol (Cimzia®), a humanized Fab-PEG conjugate of about 90 kDa, is approved and widely used in the treatment of Crohn's disease and rheumatoid arthritis.

Despite the advances in the field, there remains a need for biologics with an optimal combination of biophysical features. For example, topical treatment of skin diseases, i.e. applying TNF alpha inhibitors topically to the skin, would be a much preferred application route as the side-effects of systemic treatment could be avoided. However, to date, such treatment is not feasible, inter alia, as the currently approved immunotherapeutics are too large and hence cannot cross the skin stratum corneum and/or due to the drug production costs.

The key role of TNF alpha in psoriasis and psoriatic arthritis is well established (see, e.g., CORDORO, K M and FLEDMAN S R. TNF-alpha inhibitors in dermatology. Skin Therapy Letter 2007, vol. 12, pp. 4-6). Psoriasis is a frequent disease with a prevalence of 2-3%. While milder forms can be treated topically with glucocorticoids and/or vitamin D3-analogues, more severe forms require systemic treatment including cyclosporine, methotrexate or eventually biologics (Prieto-Pérez R. et al, Pharmacogenomics. 2013 October; 14(13):1623-1634). The introduction of biological therapies for the systemic treatment of severe psoriasis involving the use of monoclonal antibodies targeting e.g. TNF alpha (adalimumab, etanercept and infliximab) has substantially addressed the medical need of patients suffering from severe forms of psoriasis. While highly effective, these drugs are associated with a number of potentially severe and serious adverse events. Therefore, the benefit/risk profile of these drugs precludes the majority of psoriasis patients presenting with mild to moderate forms of psoriasis.

Side effects could e.g. be reduced through local application of biological drugs, i.e. topical administration. However, due to their large size, full-length antibodies are not suitable for such a route of administration.

Hidradenitis suppurativa, also termed acne inversa, is another TNF alpha related disorder. Said inflammatory chronic disease is characterized by clusters of abscesses in the apocrine gland bearing skin, such as the axilla, inner thighs, groin and buttocks (SCHEINFELD, N. Hidradenitis suppurativa: A practical review of possible medical treatments based on over 350 hidradenitis patients. Dermatol Online Journal 2013, vol 19, p.1.) TNF alpha inhibitors have successfully been used in the treatment of said orphan disease (Brunasso A M, Massone C. Treatment of hidradenitis suppurativa with tumour necrosis factor-alpha inhibitors: An update on infliximab. Acta Derm Venereol. 2011, vol. 91(1), pp.70; Sotiriou E. et al, Etanercept for the treatment of hidradenitis suppurativa, Acta Derm Venereol. 2009, vol. 89(1), pp. 82-3). Antibodies directed against TNF alpha have also been efficient in the treatment of pyoderma gangrenosum, another orphan skin disease (Reddick C L et al. Successful treatment of superficial pyoderma gangrenosum associated with hidradenitis suppurativa with adalimumab. Dermatol Online J. 2010, vol. 16(8), pp.15). To date, no biological drug has been approved for the treatment of such orphan diseases, however, commercially available biologics are used off-label.

SUMMARY

In a first aspect, a binding member for TNF alpha is provided. In some embodiments the binding member is humanized and neutralizes the activity of soluble TNF alpha. In some embodiments the binding member is a proteinaceous binding molecule with immunoglobulin-like functions specific for TNF alpha. In some embodiments the binding member is an immunoglobulin specific for TNF alpha. In some embodiments the binding member is an antibody fragment specific for TNF alpha. In some embodiments the binding member is a mammalian immunoglobulin or a fragment thereof. In some embodiments the binding member is a humanized immunoglobulin or a fragment thereof. In some embodiments the binding member is a human immunoglobulin or a fragment thereof.

In one embodiment, there is provided a monovalent binding member which inhibits soluble TNF alpha with a potency of lower than 50 picomolar (pM), as determined by measuring the half-maximum inhibitory concentration $IC_{50}$ with regard to inhibiting the biological effect of soluble human TNF alpha.

A binding member, in particular an antibody fragment, whether being humanized or not, having a potency value in the pM-range is particular, and an item not routinely obtained. This is particularly true for a monovalent antibody fragment, which includes only one variable light and heavy chain, and therefore lacks any avidity effect of a bivalent antibody that includes two light and two heavy chains.

Moreover, when converting a full-length antibody into a smaller fragment, its potency usually becomes diminished. This is not only due to the accompanying change of valency (for example, the antibody fragment might only be monovalent whereas a full-length immunoglobulin is bi- or multivalent) but may also be caused by steric reasons.

In some embodiments the binding member according to the first aspect includes a CDR sequence defined by SEQ ID Nos.: 3 to 8. The binding member includes in some embodiments two or more, preferably all CDR sequences of the group consisting of SEQ ID Nos.: 3 to 8. In some embodiments the binding member includes a CDR sequence defined by SEQ ID No: 3. In some embodiments the binding member includes a CDR sequence defined by a sequence that has at least 80% amino acid identity to SEQ ID No: 3. In some embodiments the binding member includes a CDR sequence defined by a sequence that has at least 90% amino acid identity to SEQ ID No: 3. In some embodiments the binding member includes a CDR sequence defined by SEQ ID No: 4. In some embodiments the binding member includes a CDR sequence defined by a sequence that has at least 85% amino acid identity to SEQ ID No: 4. In some embodiments the binding member includes a CDR sequence defined by SEQ ID No: 5. In some embodiments the binding member includes a CDR sequence defined by a sequence that has at least 80% amino acid identity to SEQ ID No: 5. In some embodiments the binding member includes a CDR sequence defined by a sequence that has at least 85% amino acid identity to SEQ ID No: 5. In some embodiments the binding member includes a CDR sequence defined by a sequence that has at least 93% amino acid identity to SEQ ID No: 5. In some embodiments the binding member includes a CDR sequence defined by SEQ ID No: 6. In some embodiments the binding member includes a CDR sequence defined by a sequence that has at least 80% amino acid identity to SEQ ID No: 6. In some embodiments the binding member includes a CDR sequence defined by a sequence that has at least 88% amino acid identity to SEQ ID No: 6. In some embodiments the binding member includes a CDR sequence defined by SEQ ID No: 7. In some embodiments the binding member includes a CDR sequence defined by a sequence that has at least 80% amino acid identity to SEQ ID No: 7. In some embodiments the binding member includes a CDR sequence defined by a sequence that has at least 94% amino acid identity to SEQ ID No: 7. In some embodiments the binding member includes a CDR sequence defined by a sequence that has at least 80% amino acid identity to SEQ ID No: 8. In some embodiments the binding member includes a CDR sequence defined by a sequence that has at least 92% amino acid identity to SEQ ID No: 8. In some embodiments the binding member includes three or more sequences of the group consisting of SEQ ID Nos.: 3 to 8.

In some embodiments the binding member disclosed herein includes a variable light chain framework sequence having at least 90% identity to SEQ ID No: 1; and a variable heavy chain framework sequence having at least 90% identity to SEQ ID No: 2. In some embodiments the binding member disclosed herein includes a variable light chain framework sequence having at least 97% identity to SEQ ID No: 1; and a variable heavy chain framework sequence having at least 90% identity to SEQ ID No: 2. In some embodiments the binding member disclosed herein includes a variable light chain framework sequence having at least 90% identity to SEQ ID No: 1; and a variable heavy chain framework sequence having at least 96% identity to SEQ ID No: 2.

In a preferred embodiment, the binding member is a single chain variable fragment (scFv) that includes the sequence of SEQ ID No: 9. The binding member may be a single chain variable fragment (scFv) that essentially consists of the sequence of SEQ ID No: 9. In some embodiments the binding member consists of the sequence of SEQ ID No: 9.

The binding members provided herein are highly stable, i.e., they remain monomeric and functionally active for prolonged periods of time. This applies in particular to an antibody fragment, and more particularly to a scFv as disclosed herein. Stability parameters are crucial factors for providing a viable drug. The more stable a drug, the longer the shelf half-life time. Unstable antibodies tend to dimerize or oligomerize and even precipitate, thereby decreasing shelf-life and finally becoming less suitable for pharmaceutical applications because of, e.g., increased immunogenicity. A respective binding member also remains monomeric at high concentrations, having the advantage of smaller volumes of administration.

For certain therapeutic indications, an antibody fragment provides advantages when compared to a full-length immunoglobulin, which may be attributed to its smaller size and the lack of the constant region Fc of immunoglobulin. For example, a scFv is capable of more efficiently penetrating tissue due to its small size. Furthermore, it displays a decreased retention in the systemic circulation as it is not capable of to binding to Fc receptors such as FcRn, eventually leading to higher renal clearance rates. These characteristics of good tissue penetration, with subsequent even distribution in the tissue and a rapid elimination of small antibody fragments, such as a scFv from the systemic circulation, are particularly advantageous for both chronic local/topical as well as acute systemic diseases. This practical utility has, however, been severely limited in the past by low stability and low biological potency of a scFv.

A binding member as provided herein exerts very high inhibitory potency with regard to human TNF alpha. A biologically very potent binding member is particularly useful since it allows, e.g., the administration of low amounts of drug to the patient, thereby decreasing the overall costs of treatment. In addition, a more complete neutralization of the molecular target of the disease is rendered feasible.

Moreover, different, novel application routes in animal models as well as in human therapy can be envisioned when applying highest potency binding members. For example, as to topically applied drugs (e.g., to the skin), although the delivery efficacy may be limited due to the barrier function of the stratum corneum and/or other biological structures, the efficacy of treatment is restored by the high potency of the otherwise limited quantity of drug molecules that passes such physiological barriers.

Often, the high amount of a less potent drug which needs to be administered to achieve similar pharmacodynamic effects as with a more potent drug, translates into much higher intravenous or subcutaneous application volumes. Such higher application volumes are disadvantageous for therapeutic use in animals and humans for two reasons: firstly, the impracticality of treating patients with a high volume of drug, and secondly, biologics such as an antibody molecule are expensive per unit of mass.

Lower quantities of drug required for treatment translate into lower drug production costs. In particular, antibody fragments are amenable to low production costs since the use of, e.g., bacterial or yeast culture systems generally results in lower costs when compared to mammalian expression systems, typically used for the production of a full-length immunoglobulin molecule. The combination of smaller quantities of drug to be administered and cheaper manufacturing processes opens the possibility of more cost-efficient medicines per patient. Thus, a larger number of patients may benefit from such drug.

In a second aspect there is provided a nucleic acid molecule. The nucleic acid molecule encodes a binding member according to the first aspect. The nucleic acid molecule generally contains a sequence encoding the binding member according to the first aspect. In some embodiments the nucleic acid molecule essentially consists of a sequence encoding the binding member according to the first aspect. In some embodiments the nucleic acid molecule consists of a sequence encoding the binding member according to the first aspect. The sequence encoding the binding member is in some embodiments operably linked to a regulatory region such as a promoter. The sequence encoding the binding member is in some embodiments included in an expression cassette. In some embodiments the nucleic acid molecule is an isolated nucleic acid molecule. In some embodiments the nucleic acid molecule is included in a vector.

In a third aspect there is provided a vector. The vector contains a sequence that encodes the binding member according to the first aspect. The vector may contain a sequence according to the second aspect.

In a fourth aspect there is provided a host cell. The host cell contains a nucleic acid molecule according to the second aspect. In some embodiments the host cell contains a vector according to the third aspect.

In a fifth aspect a compositions is provided. A respective composition may contain the binding member according to the first aspect, a nucleic acid molecule according to the second aspect, a vector according to the third aspect, or a host cell according to the fourth aspect. Such a composition furthermore includes a suitable carrier, diluent or excipient. Such composition may be formulated for cosmetic, diagnostic of pharmaceutical use.

In a sixth aspect, provided is a method of treating a TNF alpha-mediated disease. The method includes administering the binding member according to the first aspect to a subject in need thereof. The method generally includes administering to a subject in need thereof a pharmaceutical composition according to the fifth aspect. Typically an effective amount of the binding member is administered over a period of time. An effective amount of the binding member may thus be administered to a subject repeatedly. An effective amount of the binding member may thus be administered to a subject in multiple doses. Where multiple doses are being administered, the dosage may be constant throughout the therapy. In some embodiments the dosage may be changed, such as increased or decreased, during therapy. In some embodiments an effective amount of the binding member is administered in the form of a single dose. In some embodiments an effective amount of the binding member is administered to a subject only once.

In some embodiments the method according to the sixth aspect includes discontinuing the administration of the binding member according to the first aspect. In such embodiments the method according to the sixth aspect may include contacting a biological sample with a binding member according to the first aspect. The biological sample may be a body fluid sample. The biological sample may also be a biopsy sample. Contacting the biological sample with the binding member is carried out under conditions permissive for specific binding of the binding member to TNF alpha. The method may furthermore include detecting whether a complex between the binding member and TNF alpha has been formed. In some embodiments the method may include measuring the amount of complex formed between the binding member and TNF alpha. The method may include quantifying the amount of complex formed between the binding member and TNF alpha.

In some embodiments the amount of complex formed between the binding member and TNF alpha is compared to a threshold value. The method according to the sixth aspect may include discontinuing the administration of the binding member, and the pharmaceutical composition, respectively, if an amount of complex between the binding member and TNF alpha below the threshold value has been detected. In some embodiments the method according to the sixth aspect includes monitoring the amount of complex formed between the binding member and TNF alpha.

The method according to the sixth aspect may include continuing the administration of the binding member, and the pharmaceutical composition, respectively, if an amount of complex between the binding member and TNF alpha has been detected that is at or above the threshold value.

A binding member as described herein can, e.g., be used as medicament. A respective binding member may for instance be for use in the treatment of a TNF alpha-mediated disease. In some embodiments a binding member as described herein is used in diagnosis. A binding member as described herein can also be used in cosmetics. In some embodiments a binding member as described herein is used for detection purposes. A binding member as described herein may for instance be used in a binding assay.

Accordingly, in some embodiments, the binding member is for medical use. Put differently, the binding member may be for use as a therapeutic agent. In this regard provided is also the use of a binding agent according to the first aspect in the manufacture of a medicament. In some embodiments the use is the use of a binding agent according to the first aspect in the manufacture of a medicament for the treatment of a TNF alpha-mediated disease. In this regard provided is also a pharmaceutical composition for the treatment of a TNF alpha-mediated disease. Provided is also an agent for the treatment of a TNF alpha-mediated disease. The agent includes the binding member according to the first aspect. The agent may essentially consist of the binding member according to the first aspect.

Furthermore, a nucleic acid molecule according to the second aspect, a vector according to the third aspect or a host cell according to the fourth aspect may be used as medicament. A nucleic acid molecule according to the second aspect, a vector according to the third aspect or a host cell according to the fourth aspect may in some embodiments be for use in the treatment of a TNF alpha-mediated disease. In some embodiments a nucleic acid molecule according to the second aspect, a vector according to the third aspect or a host cell according to the fourth aspect can be used in diagnostics. A nucleic acid molecule according to the second aspect, a vector according to the third aspect or a host cell according to the fourth aspect can also be used in cosmetics. In some embodiments a nucleic acid molecule according to the second aspect, a vector according to the third aspect or a host cell according to the fourth aspect is used for detection purposes. Hence, a binding member disclosed herein—or a nucleic acid molecule encoding the same, a corresponding vector or host cell—may be used in the production of a medicament useful in the treatment of a TNF alpha-mediated disease.

In a seventh aspect a method of inhibiting the interaction between TNF alpha and TNF-R1 and/or TNF-R2 is provided. The method includes the step of providing TNF alpha and TNF-R1 and/or TNF-R2. The method furthermore includes the step of contacting TNF alpha with a binding member according to the first aspect.

In an eighth aspect provided is a method of inhibiting TNF alpha biological activity. The method includes the step of providing TNF alpha. The method also includes the step of contacting the TNF alpha with a binding member according to the first aspect.

In a ninth aspect provided is a method of producing a binding member disclosed herein. The method includes cultivating a host cell according to the fourth aspect. The method thereby includes allowing the binding member to be expressed. Thereby a reaction mixture may be formed. The method also includes recovering the binding member, for example from a respective reaction mixture formed. In some embodiments the method includes purifying the binding member.

In some embodiments, the method according to the ninth aspect may further include at least one step of chemical synthesis. The step of chemical synthesis may for example be a step of modifying the binding member once it has been obtained. An illustrative example is a post-translational modification such as a glycosylation or a PEGylation. PEGylation is the covalent attachment of one or more molecules of polyethylene glycol (PEG). In some embodiments the step of chemical synthesis introduces a lipid moiety via covalent attachment. In some embodiments the step of chemical synthesis introduces a carbohydrate moiety via covalent attachment. In some embodiments the step of chemical synthesis introduces a detectable moiety such as a radiolabel. A detectable label may also be introduced via covalent attachment.

In a tenth aspect there is provided a method of producing a binding member as disclosed herein. The method includes contacting a cell-free expression system with a nucleic acid product template. The nucleic acid product template encodes the binding member according to the first aspect. In some embodiments the method includes providing the cell-free system. The method may also include providing the nucleic acid product template. The method also includes allowing transcription and translation of the nucleic acid product template to occur. As a result, the method includes allowing a reaction mixture to be formed. Furthermore, the method includes recovering the binding member from the reaction mixture.

In some embodiments the method according to the tenth aspect includes enriching the binding member. In some embodiments the method according to the tenth aspect includes purifying the binding member. In some embodiments the method according to the tenth aspect includes isolating the binding member. In some embodiments the method includes at least one step of chemical synthesis. Accordingly, producing the binding member may include a step of chemical synthesis.

In an eleventh aspect there is provided a method of detecting the presence of TNF alpha in a biological sample. The method may be an in vivo method or an in vitro method. The method includes the step of contacting the biological sample with a binding member according to the first aspect. In some embodiments the method includes providing a binding member according to the first aspect. Contacting the biological sample with a binding member according to the first aspect is carried out under conditions permissive for specific binding of the binding member to TNF alpha. The method furthermore includes the step of detecting whether a complex between the binding member and TNF alpha has been formed.

In some embodiments the method according to the eleventh aspect may include assessing the amount of complex formed between the binding member and TNF alpha. The method may include quantifying the amount of complex formed between the binding member and TNF alpha.

In the method according to the eleventh aspect, the biological sample is generally a sample from a subject. In some embodiments the biological sample is a body fluid sample from the subject. In some embodiments the biological sample is a biopsy sample. A body fluid sample is in some embodiments a blood sample. In some embodiments a body fluid sample is a urine sample. In some embodiments a body fluid sample is a cerebrospinal fluid sample. In some embodiments a body fluid sample is a synovial fluid sample. A body fluid sample is in some embodiments a lymph sample.

In some embodiments the method according to the eleventh aspect is a method of stratifying a subject for therapy of a TNF alpha-mediated disease. The method can be taken to be a method of determining whether the subject will respond to therapy of a TNF alpha-mediated disease using the binding member disclosed herein. The method may include comparing the amount of complex formed between the binding member and TNF alpha to a threshold value. An amount of complex formed between the binding member and TNF alpha that is at or above the threshold value indicates that the subject will respond to therapy of a TNF alpha-mediated disease using the binding member. An amount of complex formed between the binding member and TNF alpha that is below the threshold value indicates that the subject will not respond to therapy of a TNF alpha-mediated disease using the binding member.

According to a twelfth aspect provided is a combination of the binding member according to the first aspect and a solution of TNF alpha of known concentration. Such a solution of TNF alpha may serve in obtaining a reference solution, for example for calibration purposes. The combination of the binding member and the solution of TNF alpha may be included in a kit. The combination of the binding member and the solution of TNF alpha may define a kit. The kit may include two containers, the first container including the binding member, the second container including the solution of TNF alpha. The kit may also essentially consist of the first container including the binding member and the second container including the solution of TNF alpha. In one embodiment the kit consists of the first container, the second container and instructions for use.

According to a thirteenth aspect there is provided a combination of the binding member according to the first aspect and a detection reagent. The kit may include two containers, the first container including the binding member, the second container including the detection reagent. In some embodiments the binding member includes a detectable label such as an enzyme. The detectable label may require the presence of a reagent. As an illustrative example, an enzyme substrate may be required, the conversion of which is being catalysed by the enzyme. The enzyme substrate may for example generate a detectable product. The respective reagent, for example an enzyme substrate, may be included in the second container.

According to a fourteenth aspect there is provided an article of manufacture, which may for instance be a kit. Such an article of manufacture may include the binding member according to the first aspect together with a packaged combination of reagents with instructions. The article of manufacture may essentially consist of the binding member and a packaged combination of reagents with instructions. In one embodiment the article of manufacture consists of the binding member and a packaged combination of reagents with instructions.

BRIEF DESCRIPTION OF THE DRAWINGS

FIG. 4 is a graph showing that scFv1 binds and neutralizes the transmembrane (tm) form of TNF alpha.

DETAILED DESCRIPTION

Figure 1A:
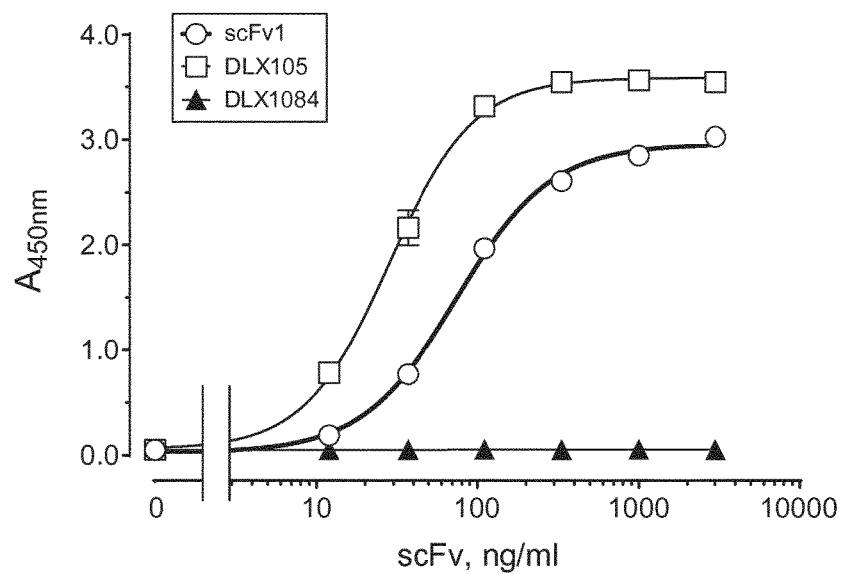
FIG. 1A is a graph showing the results of specific binding of scFvs to recombinant human (rh)TNF alpha in ELISA. scFv1 (open circle, ○), or scFv DLX105 (open square, □), serving as a positive control, were added to the immobilized rhTNF alpha at various concentrations. Bound scFvs were detected using Protein L-HRP. A scFv of a different, and thus irrelevant, specificity (DLX1084) was used as a negative control (closed triangle, ▲).

In order that the explanations on the binding members, nucleic acids, vectors, host cells, compositions, methods and uses disclosed herein may be more readily understood, certain terms are first defined.

Definitions

Unless otherwise defined, all other scientific and technical terms used in the description, figures and claims have their ordinary meaning as commonly understood by one of ordinary skill in the art. Although similar or equivalent methods and materials to those described herein can be used in the practice or testing of the binding members, nucleic acids, vectors, host cells, compositions, methods and uses disclosed herein, suitable methods and materials are described below. All publications, patent applications, patents, and other references mentioned herein are incorporated by reference in their entirety. In case of conflict, the present specification, including definitions, will prevail. The materials, methods, and examples are illustrative only and not intended to be limiting.

The word "about" as used herein refers to a value being within an acceptable error range for the particular value as determined by one of ordinary skill in the art, which will depend in part on how the value is measured or determined, i.e., the limitations of the measurement system. For example, "about" can mean within one, or more than one standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "administering", as used herein, refers to any mode of transferring, delivering, introducing, or transporting matter such as a compound, e.g. a pharmaceutical compound, or other agent such as an antigen, to a subject. Modes of administration include oral administration, topical contact, intravenous, intraperitoneal, intramuscular, intranasal, or subcutaneous administration (cf. below). Administration "in combination with" further matter such as one or more therapeutic agents includes simultaneous (concurrent) and consecutive administration in any order.

The word "assay" as used in this document refers to a method, generally known in the art, to analyse a feature, e.g. a catalytic activity, the presence, the formation or the amount of matter occurring in a biological specimen. Such matter may be occurring in a living organism or representing a living organism, such as a protein, a nucleic acid, a lipid, a cell, a virus, a saccharide, a polysaccharide, a vitamin or an ion, to name a few examples. The word "assay" emphasizes that a certain procedure or series of procedures is followed, which may be taken to represent the respective assay. An assay may include quantitated reagents and established protocols to assess the presence, absence, amount or activity of a biological entity.

The term "binding assay" generally refers to a method of determining the interaction of matter. Hence, some embodiments of a binding assay can be used to qualitatively or quantitatively determine the ability of matter, e.g. a substance, to bind to other matter, e.g. a protein, a nucleic acid or any other substance. Some embodiments of a binding assay can be used to analyse the presence and/or the amount of matter on the basis of binding of the matter to a reagent such as a binding partner that is used in the method/assay. As an illustrative example, a TNF alpha binding assay may include the use of a binding partner such as a binding member disclosed herein that specifically binds to TNF alpha. Where a binding assay is based on the use of an immunoglobulin or a proteinaceous binding molecule with immunoglobulin-like functions as a binding partner, such a method/procedure may also be called an "immunoassay". In this regard, it is understood that the signals obtained from an immunoassay are a direct result of complexes formed between one or more immunoglobulins or proteinaceous binding molecules with immunoglobulin-like functions and the corresponding analyte, such as TNF alpha, containing the necessary epitope(s) to which the binding partner(s) bind(s). While such an assay may detect the full length analyte and the assay result be expressed as a concentration of a biomarker of interest, the signal from the assay is actually a result of all such "immunoreactive" molecules present in the sample. The amount and/or presence of an analyte may also be determined by means other than an immunoassay, including protein measurements such as dot blots, Western blots, chromatographic methods, mass spectrometry, and nucleic acid measurements such as mRNA quantification.

As used herein, the terms "conservative modification" and "conservative substitution" refer to a modification and a substitution, respectively, that maintains physically, biologically, chemically or functionally the properties with regard to the corresponding reference. A molecule that includes a sequence with conservative substitution for instance has a similar size, shape, electric charge, chemical properties, including a comparable ability to form covalent or hydrogen bonds, and/or comparable polarity. Such conservative modifications include, but are not limited to, one or more nucleobases and amino acid substitutions, additions and deletions.

For example, conservative amino acid substitutions include those in which the amino acid residue is replaced with an amino acid residue having a similar side chain. For example, amino acid residues being non-essential with regard to binding to an antigen can be replaced with another amino acid residue from the same side chain family, e.g. serine may be substituted for threonine. Amino acid residues are usually divided into families based on common, similar side-chain properties, such as:

1. nonpolar side chains (e.g., glycine, alanine, valine, leucine, isoleucine, methionine),
2. uncharged polar side chains (e.g., asparagine, glutamine, serine, threonine, tyrosine, proline, cysteine, tryptophan),
3. basic side chains (e.g., lysine, arginine, histidine, proline),
4. acidic side chains (e.g., aspartic acid, glutamic acid),
5. beta-branched side chains (e.g., threonine, valine, isoleucine) and
6. aromatic side chains (e.g., tyrosine, phenylalanine, tryptophan, histidine).

This classification can be further segmented. As a further orientation, the following eight groups each contain amino acids that can typically be taken to define conservative substitutions for one another:

1) Alanine (Ala), Glycine (Gly);
2) Aspartic acid (Asp), Glutamic acid (Glu);
3) Asparagine (Asn), Glutamine (Gln);
4) Arginine (Arg), Lysine (Lys);
5) Isoleucine (Ile), Leucine (Leu), Methionine (Met), Valine (Val);
6) Phenylalanine (Phe), Tyrosine (Tyr), Tryptophan (Trp);
7) Serine (Ser), Threonine (Thr); and
8) Cysteine (Cys), Methionine (Met).

A conservative substitution can be taken to be a substitution of a first amino acid within one of the six groups above by a further amino acid within the same group of the six groups. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. A conservative substitution may also involve the use of a non-natural amino acid.

Non-conservative substitutions, i.e. exchanging members of one family against members of another family, may lead to substantial changes, e.g., with respect to the charge, dipole moment, size, hydrophilicity, hydrophobicity or conformation of the binding member, which may lead to a significant drop in the binding activity, in particular if amino acids are affected that are essential for binding to the target molecule. A non-conservative substitution may also involve the use of a non-natural amino acid.

Conservative and non-conservative modifications can be introduced into parental binding members by a variety of standard techniques known in the art, such as combinatorial chemistry, site-directed DNA mutagenesis, PCR-mediated and/or cassette mutagenesis, peptide/protein chemical synthesis, chemical reaction specifically modifying reactive groups in the parental binding member. The variants can be tested by routine methods for their chemical, biological, biophysical and/or biochemical properties. Preferably, the conservative amino acid substitution does not substantially change the functional, and generally also the structural characteristics of the parental sequence. Accordingly, the binding characteristics of a binding member that includes a conservative substitution are at least essentially unaltered. Furthermore, a conservative amino acid substitution does generally not substantially modify or disrupt a secondary structure of the parental sequence.

The term "detectable label" is used to herein to refer to any substance the detection or measurement of which, either directly or indirectly, by physical or chemical means, is indicative of the presence of a selected target bioentity in a sample. Representative examples of useful detectable labels include, but are not limited to, molecules or ions directly or indirectly detectable based on light absorbance, fluorescence, reflectivity, light scatter, phosphorescence, or luminescence properties, molecules or ions detectable by their radioactive properties or molecules or ions detectable by their nuclear magnetic resonance or paramagnetic properties. A detectable label may in some embodiments be a molecule that can be indirectly detected based on light absorbance or fluorescence, for example, various enzymes which cause appropriate substrates to convert, e.g., from non-light absorbing to light absorbing molecules, or from non-fluorescent to fluorescent molecules.

An "effective amount" or a "therapeutically effective amount" of an item such as a compound, including a binding member disclosed herein, is an amount—either as a single dose or as part of a series of doses—which at the dosage regimen applied yields the desired therapeutic effect, i.e., to reach a certain treatment goal. A therapeutically effective amount is generally an amount sufficient to provide a therapeutic benefit in the treatment or management of the relevant pathological condition, or to delay or minimize one or more symptoms associated with the presence of the condition. The dosage will depend on various factors including patient and clinical factors (e.g., age, weight, gender, clinical history of the patient, severity of the disorder and/or response to the treatment), the nature of the disorder being treated, the particular composition to be administered, the route of administration, and other factors.

An "epitope" is antigenic and thus an epitope may also be taken to define an "antigenic structure" or "antigenic determinant". Thus, a binding domain of an immunoglobulin or of a proteinaceous binding molecule with immunoglobulin-like functions is an "antigen-interaction-site". The term "antigen-interaction-site" defines, in accordance with the present specification, a motif of a polypeptide, which is able to specifically interact with a specific antigen or a specific group of antigens, e.g. TNF alpha in different species. This binding/interaction is also understood to define a "specific recognition". An epitope usually consists of spatially accessible surface groupings of moieties of one or more chemical entities such as polypeptide chains or mono- or polysaccharides. Surface groupings defining an epitope may for instance be groupings of amino acids or sugar side chains. An epitope usually has specific three dimensional structural characteristics, as well as specific charge characteristics. Conformational and nonconformational epitopes are distinguished in that the binding to the former but not the latter is lost in the presence of denaturing solvents.

The term "epitope" also refers to a site on an antigen such as TNF alpha, with which an immunoglobulin, a T cell receptor or a proteinaceous binding molecule with immunoglobulin-like functions forms a complex. In some embodiments, an epitope is a site on a molecule against which an immunoglobulin or a proteinaceous binding molecule with immunoglobulin-like functions will be produced and/or to which an antibody will bind. For example, an epitope can be recognized by an immunoglobulin or a proteinaceous binding molecule with immunoglobulin-like functions. The epitope may be a "linear epitope", which is an epitope where an amino acid primary sequence contains the epitope recognized. A linear epitope typically includes at least 3, and more usually, at least 5 amino acids in a unique sequence. A linear epitope may for example include about 8 to about 10 amino acids in a unique sequence. The epitope may also be a "conformational epitope", which in contrast to a linear epitope, is an epitope where the primary sequence of the amino acids that includes the epitope is not the sole defining component of the epitope recognized (e.g., an epitope wherein the primary sequence of amino acids is not necessarily recognized by the antibody defining the epitope). Typically a conformational epitope includes a larger number of amino acids than a linear epitope. With regard to recognition of conformational epitopes, an immunoglobulin or a proteinaceous binding molecule with immunoglobulin-like functions recognizes a 3-dimensional structure of the antigen, such as a peptide or protein, or a fragment of a peptide or protein. As an illustrative example, when a protein molecule folds to form a three dimensional structure, certain amino acids and/or all or portions of the polypeptide backbone forming the conformational epitope become juxtaposed, allowing an antibody to recognize the epitope. Methods of determining conformation of epitopes include, but are not limited to, x-ray crystallography, 2-dimensional nuclear magnetic resonance spectroscopy, site-directed spin labeling and electron paramagnetic resonance spectroscopy.

By the use of the term "enriched" in reference to a polypeptide, a nucleic acid or a cell is meant that the specific amino acid/nucleotide sequence or cell, including cell population, constitutes a significantly higher fraction (2-5 fold) of the total amino acid sequences or nucleic acid sequence present in the sample of interest than in the natural source from which the sample was obtained. The polypeptide, a nucleic acid or a cell may also constitute a significantly higher fraction than in a normal or diseased organism or than in normal or diseased cells or in the cells from which the sequence was taken. This could be caused by preferential reduction in the amount of other amino acid/nucleotide sequences or cells present, or by a preferential increase in the amount of the specific amino acid/nucleotide sequence or cell of interest, or by a combination of the two. However, it should be noted that enriched does not imply that there are no other amino acid sequences, nucleotide sequences or cells present. The term merely defines that the relative amount of the sequence of interest has been significantly increased. The term significant here is used to indicate that the level of increase is useful to the person achieving such an increase, and generally means an increase relative to other amino acid or nucleic acid sequences of about at least 2-fold, for example at least about 5- to 10-fold or even more. The term is meant to cover only those situations in which man has intervened to increase the proportion of the desired amino acid sequence, nucleotide sequence or cell.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The terms "expressing" and "expression" in reference to a biomarker are intended to be understood in the ordinary meaning as used in the art. A peptide/protein is expressed by a cell via transcription of a nucleic acid into mRNA, followed by translation into a polypeptide, which is folded and possibly further processed. Hence, the statement that a cell is expressing a peptide/protein implies that the peptide/protein has been synthesized by the expression machinery of the respective cell.

The term "expression cassette" refers to a coding sequence and a promoter, optionally in combination with one or more control sequences. Expression cassettes for enzymes include, for example and without limitation, a translation initiation control sequence.

The term "control sequence" refers to nucleic acid sequences in a gene or expression cassette that regulate transcription of a coding sequence and so include promoters, enhancers, transcription termination sequences, and translation initiation sequences.

With regard to the respective biological process itself, the terms "expression", "gene expression" or "expressing" refer to the entirety of regulatory pathways converting the information encoded in the nucleic acid sequence of a gene first into messenger RNA (mRNA) and then to a protein. Accordingly, the expression of a gene includes its transcription into a primary hnRNA, the processing of this hnRNA into a mature RNA and the translation of the mRNA sequence into the corresponding amino acid sequence of the protein. In this context, it is also noted that the term "gene product" refers not only to a protein, including e.g. a final protein (including a splice variant thereof) encoded by that gene and a respective precursor protein where applicable, but also to the respective mRNA, which may be regarded as the "first gene product" during the course of gene expression.

Within the scope of the present disclosure, the term "antibody" refers to a full-length immunoglobulin as well as to a fragment thereof. Such a full-length immunoglobulin may be monoclonal, polyclonal, chimeric, humanized, veneered or a human antibody. An antibody as disclosed herein may in some embodiments be glycosylated. In some embodiments an antibody as disclosed herein may not be glycosylated.

By "fragment" in reference to a polypeptide such as an immunoglobulin or a proteinaceous binding molecule is meant any amino acid sequence present in a corresponding polypeptide, as long as it is shorter than the full length sequence and as long as it is capable of performing the function of interest of the protein—in the case of an immunoglobulin specifically binding to the desired target, e.g. antigen (TNF alpha, for example). The term "antibody fragment" refers to a portion of an immunoglobulin, often the hypervariable region and portions of the surrounding heavy and light chains that displays specific binding affinity for a particular target, typically a molecule. A hypervariable region is a portion of an immunoglobulin that physically binds to the polypeptide target. An antibody fragment thus includes or consists of one or more portions of a full-length immunoglobulin retaining the targeting specificity of the immunoglobulin. Such antibody fragment may for instance lack at least partially the constant region (Fc region) of the full-length immunoglobulin. In some embodiments, an antibody fragment is produced by digestion of the full-length immunoglobulin. An antibody fragment may also be a synthetic or recombinant construct that contains one or more parts of the immunoglobulin or immunoglobulin chains (see e.g. HOLLIGER, P. and Hudson, J. Engineered antibody fragments and the rise of single domains. *Nature Biotechnology* 2005, vol. 23, no. 9, p. 1126-1136). Examples of an antibody fragment include, but are not limited to, an scFv, a Fab, a Fv, a Fab', a F(ab')$_2$ fragment, a dAb, a VHH, a nanobody, a V(NAR) or a so called minimal recognition unit.

A "single chain variable fragment" or a "single chain antibody" or an "scFv" are examples of a type of antibody fragment. An scFv is a fusion protein that includes the VH and VL domains of an immunoglobulin connected by a linker. It thus lacks the constant Fc region present a full-length immunoglobulin.

A "binding member" as used herein refers to a full-length immunoglobulin, an antibody fragment, a proteinaceous non-immunoglobulin scaffold, and/or other binding compound, which has an immunoglobulin-like function. Typically the binding member is a proteinaceous binding molecule. Such binding member can be monovalent or multivalent, i.e. having one or more antigen binding sites. Non-limiting examples of monovalent binding members include scFv, Fab fragments, dAb, VHH, DARPins, affilins and nanobodies. A multivalent binding member can have two, three, four or more antigen binding sites whereby one or more different antigens can be recognized. Full-length immunoglobulins, F(ab')$_2$ fragments, bis-scFv (or tandem scFv) and diabodies are non-limiting examples of multivalent binding members; in the exemplary multivalent binding members, two binding sites are present, i.e. the binding member is bivalent.

In some embodiments, the multivalent binding member is bispecific, i.e. the binding member is directed against two different targets or two different target sites on one target molecule. Bispecific antibodies are, e.g., reviewed in MÜLLER, D. and Kontermann, R. E. Bispecific antibodies. Edited by DÜBEL, S. Weinheim: Wiley-VCH, 2007. ISBN 3527314539. p. 345-378. In some embodiments, the multivalent binding member includes more than two, e.g., three or four different binding sites for three or four, respectively, different antigens. Such binding member is multivalent and multispecific, in particular tri- or tetra-specific, respectively.

"Non-antibody scaffolds" are antigen-binding polypeptides which are e.g. described in FIELDER, M. and Skerra, A. Non-antibody scaffolds. Edited by DÜBEL, S. Weinheim: Wiley-VCH, 2007. ISBN 3527314539. p. 467-500; or GILBRETH, R. N. and Koide, S. Structural insights for engineering binding proteins based on non-antibody scaffolds. *Curr Opin Struct Biol* 2012, vol. 22, p. 413-420. Non-limiting examples include affibodies, affilin molecules, an AdNectin, a mutein based on a polypeptide of the lipocalin family (Anticalin®), a DARPin, Knottin, a Kunitz-type domain, an Avimer, a Tetranectin and a trans-body. Avimers contain so called A-domains that occur as strings of multiple domains in several cell surface receptors (Silverman, J., et al., *Nature Biotechnology* (2005) 23, 1556-1561). Tetranectins, derived from the respective human homotrimeric protein, likewise contain loop regions in a C-type lectin domain that can be engineered for desired binding (ibid.).

"Binding compounds" are chemical or biological molecules that bind to a target and that do not belong to the class of full-length immunoglobulins, antibody fragments and non-antibody scaffolds as defined above. Examples of binding compounds, without being limited to, include macrolides (GUNDLURU, M. K. et al. Design, synthesis and initial biological evaluation of a novel pladienolide analog scaffold. *Medchemcomm.* 2011, vol. 2, p. 904-908;

PATERSON, I. et al. Total synthesis and biological evaluation of a series of macrocyclic hybrids and analogies of the antimitotic natural products dictyostatin, discodermolide and taxol. *Chem Asian J.* 2011, vol. 6, p. 459-473; MORITA, H. et al. Synthesis of unnatural alkaloid scaffolds by exploiting plant polyketide synthase. *PNAS* 2011, vol. 108, p. 13504-13509), molecular imprinted polymers (HOSHINO, Y. et al. Recognition, neutralization and clearance of target peptides in the blood stream of living mice by molecular imprinted polymer nanoparticles: a plastic antibody. *J. Am Chem Soc,* 2010, vol. 19, p. 664-6645), aptamers (STREHLITZ, B., et al. Aptamers for pharmaceuticals and their application in environmental analytics. *Bioanal Rev* 2012, vol. 4, p. 1-30; YE, M. et al. Generating Aptamers by Cell-SELEX for Applications in Molecular Medicine. *Int J Mol Sci* 2012, vol. 13, p. 3341-3353), Spiegelmers (see e.g., MAASCH, C. et al. Polyethylenimine-Polyplexes of Spiegelmer NOX-A50 directed against intracellular high mobility group protein A1 (HMGA1) reduce tumor growth in vivo. *JBC* 2010, vol. 285, p. 40012-40018), or peptides (cyclic or linear; see, e.g., GOULD, A. et al. Cyclotides, a novel ultrastable polypeptide scaffold for drug discovery. *Curr Pharm Des.* 2011, vol. 17, p. 4294-4307). Peptoids, which can act as protein ligands, are oligo(N-alkyl) glycines that differ from peptides in that the side chain is connected to the amide nitrogen rather than the $\alpha$ carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509).

A binding member as disclosed herein may be PEGylated or hyperglycosylated if desired, see also below. In some embodiments a binding member is a fusion protein of one of the exemplary proteinaceous binding molecules above and an albumin-binding domain, for instance an albumin-binding domain of streptococcal protein G. In some embodiments a binding member is a fusion protein of an immunoglobulin fragment, such as a single-chain diabody, and an immunoglobulin binding domain, for instance a bacterial immunoglobulin binding domain. As an illustrative example, a single-chain diabody may be fused to domain B of staphylococcal protein A as described by Unverdorben et al. (Protein Engineering, Design & Selection [2012] 25, 81-88).

The "$IC_{50}$" or "half-maximum inhibitory concentration" is a measure of antagonist potency and describes quantitatively the effectiveness of a compound to inhibit a biological or biochemical function. This value accordingly indicates how much of a certain item, such as a binding member, is needed to inhibit by 50% a certain biological or biochemical process or function. Although no direct indicator of affinity, the $IC_{50}$ and the $K_i$ values are correlated and can be determined via the Cheng-Prusoff equation (CHENG Y. and Prusoff W. H. Relationship between the inhibition constant (Ki) and the concentration of inhibitor which causes 50 per cent inhibition (IC50) of an enzymatic reaction. *Biochem Pharmacol* 1973, vol. 22, p. 3099-3108; RAMMES, G., et al. Identification of a domain which affects kinetics and antagonistic potency of clozapine at 5-HT3 receptors. *PLOS one* 2009, vol. 4, p. 1-14; ZHEN, J., et al. Concentration of receptor and ligand revisited in a modified receptor binding protocol for high-affinity radioligands: [$^3$H] spiperone binding to $D_2$ and $D_3$ dopamine receptors. *J Neurosci Methods* 2010, vol. 188, p. 32-38).

The term "framework" (FR) refers to the scaffold of the variable immunoglobulin domain, either the variable light chain (VL) or variable heavy chain (VH), embedding the respective CDRs. A VL and/or VH framework typically includes four framework sections, FR1, FR2, FR3 and FR4, flanking the CDR regions. Thus, as known in the art, a VL has the general structure: (FR-L1)-(CDR-L1)-(FR-L2)-(CDR-L2)-(FR-L3)-(CDR-L3)-(FR-L4), whereas a VH has the general structure: (FR-H1)-(CDR-H1)-(FR-H2)-(CDR-H2)-(FR-H3)-(CDR-H3)-(FR-H4).

The term "CDR" refers to the hypervariable regions of the antibody which mainly contribute to antigen binding. Typically, an antigen binding site includes six CDRs, embedded into a framework scaffold. Herein, the CDRs of the VL are referred to as CDR-L1, CDR-L2 and CDR-L3 whereas the CDRs of the VH are referred to as CDR-H1, CDR-H2 and CDR-H3. These can be identified as described in KABAT, E. A., et al. Sequences of Proteins of Immunological Interest. 5th edition. Edited by U.S. DEPARTMENT OF HEALTH AND HUMAN SERVICES. NIH Publications, 1991. p. 91-3242. CDR-H1 as used herein, however, differs from the Kabat definition in that it starts with position 27 and ends prior to position 36 (see FIG. 5 for illustration).

As used herein, the numbering system to identify amino acid residue positions in the VH and VL of the antibody corresponds to the "AHo"-system described by HONEGGER, A. and Plückthun, A. Yet another numbering scheme for immunoglobulin variable domains: An automatic modelling and analysis tool. *JMB* 2001, vol. 309, p. 657-670. The publication further provides conversion tables between the AHo and the Kabat system (KABAT, E. A., et al. Sequences of Proteins of Immunological Interest. 5$^{th}$ edition. Edited by U.S. DEPARTMENT OF HEALTH AND HUMAN SERVICES. NIH Publications, 1991. p. 91-3242).

"Humanized" antibodies refer to antibodies that include one or more, typically all six CDR regions of a non-human parent antibody or variants thereof or synthetic CDRs, and of which the framework is, e.g., (i) a human framework, potentially including one or more framework residues of the non-human parent antibody, or (ii) a framework from a non-human antibody modified to increase similarity to naturally produced human frameworks. Methods of humanizing antibodies are known in the art, see e.g. LEGER, O. and Saldanha, J. Antibody Drug Discovery. Edited by WOOD, C. London: Imperial College Press, 2011. ISBN 1848166281. p.1-23.

The terms "immunize", "immunization", or "immunizing" refer to exposing the immune system of an animal to an antigen or to an epitope thereof as illustrated in more detail below. The antigen may be introduced into the animal using a desired route of administration, such as injection, inhalation or ingestion. Upon a second exposure to the same antigen, the adaptive immune response, in particular T cell and B cell responses, is enhanced.

The term "isolated" indicates that matter such as a peptide or a nucleic acid molecule has been removed from its normal physiological environment, e.g. a natural source, or that a peptide or nucleic acid is synthesized. Use of the term "isolated" indicates that a naturally occurring sequence has been removed from its normal cellular (i.e., chromosomal) environment. Thus, the sequence may be in a cell-free solution or placed in a different cellular environment. By "isolated" in reference to a polypeptide or nucleic acid molecule is meant a polymer of amino acids (2 or more amino acids) or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free, e.g. about 90-95% pure or more, of e.g. non-amino acid material and/or non-nucleic acid material, respectively, naturally associated with it.

The term "identity" as used herein refers to the sequence match between two proteins or nucleic acids. The protein or nucleic acid sequences to be compared are aligned to give maximum identity, for example using bioinformatics tools such as EMBOSS Needle (pair wise alignment; available at www.ebi.ac.uk). When the same position in the sequences to be compared is occupied by the same nucleobase or amino acid residue, then the respective molecules are identical at that very position. Accordingly, the "percent identity" is a function of the number of matching positions divided by the number of positions compared and multiplied by 100%. For instance, if 6 out of 10 sequence positions are identical, then the identity is 60%. The percent identity between two protein sequences can, e.g., be determined using the Needleman and Wunsch algorithm (NEEDLEMAN, S. B. and Wunsch, C. D. A general method applicable to the search for similarities in the amino acid sequence of two proteins. *JMB* 1970, vol. 48, p. 443-453) which has been incorporated into EMBOSS Needle, using a BLOSUM62 matrix, a "gap open penalty" of 10, a "gap extend penalty" of 0.5, a false "end gap penalty", an "end gap open penalty" of 10 and an "end gap extend penalty" of 0.5. Two molecules having the same primary amino acid or nucleic acid sequence are identical irrespective of any chemical and/or biological modification. For example, two antibodies having the same primary amino acid sequence but different glycosylation patterns are identical by this definition. In case of nucleic acids, for example, two molecules having the same sequence but different linkage components such as thiophosphate instead of phosphate are identical by this definition.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu, B., et al., J. Am. Chem. Soc. (2004) 126, 4076-4077). LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in nucleic acids used in the methods disclosed in this specification. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

As used in this document, the expression "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The terms "polypeptide" and "protein" refer to a polymer of amino acid residues and are not limited to a certain minimum length of the product. Where both terms are used concurrently, this twofold naming accounts for the use of both terms side by side in the art.

The term "preventing" in the medical/physiological context, i.e. in the context of a physiological state, refers to decreasing the probability that an organism contracts or develops an abnormal condition.

The term "purified" is understood to be a relative indication in comparison to the original environment of a binding member, thereby representing an indication that the binding member is relatively purer than in the natural environment. It therefore includes, but does not only refer to, an absolute value in the sense of absolute purity from other proteinaceous binding molecules with immunoglobulin-like function, immunoglobulins or antibody fragments. Compared to the original level, the level after purifying the binding member will generally be at least 2-5 fold greater (e.g., in terms of mg/ml). Purification of at least one order of magnitude, such as about two or three orders, including for example about four or five orders of magnitude is expressly contemplated. It may be desired to obtain the binding member at least essentially free of contamination, in particular free of other proteinaceous matter, at a functionally significant level, for example about 90%, about 95%, or 99% pure. With regard to other matter such as a nucleic acid molecule, a peptide or a protein, or a cell, the above applies mutatis mutandis.

"Similar" protein sequences are those which, when aligned, share similar amino acid residues and most often, but not mandatorily, identical amino acid residues at the same positions of the sequences to be compared. Similar amino acid residues are grouped by chemical characteristics of the side chains into families. These families are described below for "conservative amino acid substitutions". The "percent similarity" between sequences is the number of positions that contain identical or similar residues at the same sequence positions of the sequences to be compared divided by the total number of positions compared and multiplied by 100%. For instance, if 6 out of 10 sequence positions have identical amino acid residues and 2 out of 10 positions contain similar residues, then the sequences have 80% similarity. The similarity between two sequences can e.g. be determined using EMBOSS Needle.

The term "specific" as used in this document is understood to indicate that a binding member is directed against, binds to, or reacts with a defined target, such as a TNF alpha. Thus, being directed to, binding to or reacting with includes that the binding member specifically binds to TNF alpha. The term "specifically" in this context means that the binding member reacts with TNF alpha, or/and a portion thereof, but at least essentially not with another protein. The term "another protein" includes any protein, including proteins closely related to or being homologous to e.g. TNF alpha against which the binding member is directed to. The term "does not essentially bind" means that the binding member does not have particular affinity to another protein, i.e., shows a cross-reactivity of less than about 30%, when compared to the affinity to TNF alpha. In some embodiments the binding member shows a cross-reactivity of less than about 20%, such as less than about 10%. In some embodiments the binding member shows a cross-reactivity of less than about 9, 8, or 7%, when compared to the affinity to TNF alpha. In some embodiments the binding member shows a cross-reactivity of less than about 6%, such as less than about 5%, when compared to the affinity to TNF alpha. Whether the binding member specifically reacts as defined herein above can easily be tested, inter alia, by comparing the reaction of a respective binding member with TNF alpha, and the reaction of the binding member with (an) other protein(s). The term "specifically recognizing", which can be used interchangeably with the terms "directed to" or "reacting with" means in the context of the present disclosure that a particular molecule, generally an immunoglobulin, an immunoglobulin fragment or a proteinaceous binding molecule with immunoglobulin-like functions is capable of specifically interacting with and/or binding to at least two, including at least three, such as at least four or even more amino acids of an epitope as defined herein. Generally the immunoglobulin or proteinaceous binding molecule can thereby form a complex with the respective epitope of e.g. TNF alpha. Such binding may be exemplified by the specificity of a "lock-and-key-principle". "Specific binding" can also be determined, for example, in accordance with a Western blot, ELISA-, RIA-, ECL-, IRMA-test, FACS, IHC and a peptide scan.

The terms "stratifying" and "stratification" as used herein indicate that an individual is assigned to a certain group according to characteristics matching the respective group such as a corresponding probability of responding to a binding member disclosed herein. The groups may be, for example, for testing, prescribing, suspending or abandoning a binding member. Accordingly, in some embodiments of a method or use according to the invention a subject may be stratified into a subgroup of a clinical trial of a therapy.

The term "subject" as used herein, also addressed as an individual, refers to a human or non-human animal, generally a mammal. A subject may be a mammalian species such as a rabbit, a mouse, a rat, a Guinea pig, a hamster, a dog, a cat, a pig, a cow, a goat, a sheep, a horse, a monkey, an ape or a human. Thus, the methods, uses and compositions described in this document are applicable to both human and veterinary disease. As explained in more detail below, the sample has been obtained from the subject. It is thus understood that conclusions drawn from expression levels in the sample and decisions based thereon concern the subject from whom/which the sample has been taken. Further, while a subject is typically a living organism, a method or use described in this document may also be used in post-mortem analysis. Where the subject is a living human who is receiving medical care for a disease or condition, it is also addressed as a "patient".

The terms "treatment" and "treating" as used herein, refer to a prophylactic or preventative measure having a therapeutic effect and preventing, slowing down (lessen), or at least partially alleviating or abrogating an abnormal, including pathologic, condition in the organism of a subject. Treatment according to the present disclosure involves the administration of a pharmaceutically effective amount of a molecule as described herein, i.e. inter alia, the binding member (such as an antibody), nucleic acid, vector or host cell disclosed herein, to a subject in need thereof to prevent, cure, delay the onset and/or progression, reduce the severity of, stabilize, modulate, cure or ameliorate one or more symptoms of an TNF alpha-related disorder. Typically, the binding member, nucleic acid, vector or host cell is provided in a pharmaceutical composition including those described herein. Those in need of treatment include those already with the disorder as well as those prone to having the disorder or those in whom the disorder is to be prevented (prophylaxis). Generally a treatment reduces, stabilizes, or inhibits progression of a symptom that is associated with the presence and/or progression of a disease or pathological condition. The term "administering" relates to a method of incorporating a compound into cells, body fluid or tissue of a subject. The term "therapeutic effect" refers to the inhibition or activation of factors causing or contributing to the abnormal condition. A therapeutic effect relieves to some extent one or more of the symptoms of an abnormal condition or disease. The term "abnormal condition" refers to a function in the cells or tissues of an organism that deviates from their normal functions in that organism.

The term "TNF alpha specific binding" as used herein specifies that a binding member binds to TNF alpha with higher affinity than to a structurally different antigen which does not contain the TNF alpha epitope to which the anti-TNF alpha binding member binds. Specific binding is reflected by a dissociation equilibrium constant ($K_D$) of lower than 1 micromolar. This constant can be determined, e.g. using Quartz Crystal Microbalance (QCM) in an Attana instrument, or Surface Plasmon Resonance (SPR) technology in a BIACORE instrument.

As used herein, "hTNF alpha" refers to human TNF alpha and includes natural hTNF alpha and rhTNF alpha. "rTNF alpha" refers to recombinant TNF alpha. Recombinant TNF alpha may or may not have an amino terminal methionine residue, depending upon the method by which it is prepared. "rhTNF alpha" beta refers to recombinant human TNF alpha. rhTNF alpha may, e.g., be obtained from Peprotech, USA, cat. no. 300-01A. TNF alpha may also be obtained by isolation from biological samples of human or non-human origin.

A "variant" refers to an amino acid or nucleic acid sequence which differs from the parental sequence by virtue of addition (including insertions), deletion and/or substitution of one or more amino acid residues or nucleobases while retaining at least one desired activity of the parent sequence disclosed herein. In the case of antibodies such desired activity may include specific antigen binding. Similarly, a variant nucleic acid sequence may be modified when compared to the parent sequence by virtue of addition, deletion and/or substitution of one or more nucleobases, but the encoded antibody retains the desired activity as described above. Variants may be naturally occurring, such as allelic or splice variants, or may be artificially constructed.

Nucleic acid hybridization reactions can be performed under conditions of different stringency. "Stringent conditions" are widely known and published in the art. Typically, during the hybridization reaction a SSC-based buffer can be used in which SSC is 0.15 M NaCl and 15 mM citrate buffer having a pH of 7.0. Increasing buffer concentrations and the presence of a denaturing agent increase the stringency of the hybridization step. For example, high stringency hybridization conditions can involve the use of (i) 50% (vol/vol) formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/mL), 0.1% SDS, and 10% dextran sulfate at 42° C. with washes at 42° C. in 0.2× SSC and 0.1% SDS; (ii) 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C., or (iii) 10% dextran sulfate, 2× SSC, and 50% formamide at 55° C., followed by a high-stringency wash consisting of 0.1× SSC containing EDTA at 55° C. Additionally or alternatively, one, two or more washing steps using wash solutions of low ionic strength and high temperature can be included in the hybridization protocol using, for example, 0.015 M sodium chloride/0.0015 M sodium citrate/0.1% sodium dodecyl sulfate at 50° C.

The scope and meaning of any use of a term will be apparent from the specific context in which the term is used. Certain further definitions for selected terms used throughout this document are given in the appropriate context of the detailed description, as applicable.

The terms "comprising", "including," "containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to a "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable.

Various aspects of the disclosure are described in further detail in the following subsections. It is understood that the various embodiments, preferences and ranges may be combined at will. Further, depending of the specific embodiment, selected definitions, embodiments or ranges may not apply.

Binding Member/Antibody Characterization

The binding member provided herein is in some embodiments a proteinaceous binding molecule specific for TNF alpha. The proteinaceous binding molecule generally has an immunoglobulin-like function. In some embodiments the binding member essentially consists of a proteinaceous binding molecule specific for TNF alpha. In some embodiments the binding member includes a proteinaceous binding molecule specific for TNF alpha. In some embodiments the binding member is an antibody fragment specific for TNF alpha. In some embodiments the binding member essentially consists of an antibody fragment specific for TNF alpha. In some embodiments the binding member includes an antibody fragment specific for TNF alpha. The binding member is in some embodiments a full-length immunoglobulin molecule specific for TNF alpha. In some embodiments the binding member essentially consists of a full-length immunoglobulin molecule specific for TNF alpha. In some embodiments the binding member includes a full-length immunoglobulin molecule specific for TNF alpha. The binding member is in some embodiments a non-immunoglobulin scaffold specific for TNF alpha. The non-immunoglobulin scaffold generally has an immunoglobulin-like function. In some embodiments the binding member essentially consists of a non-immunoglobulin scaffold specific for TNF alpha. In some embodiments the binding member includes a non-immunoglobulin scaffold specific for TNF alpha.

The binding member has a binding specificity to TNF alpha, i.e. it specifically binds to TNF alpha. In some embodiments the binding member only binds specifically to TNF alpha, and not to any additional target. In some embodiments the binding member is bispecific in that it binds specifically to TNF alpha, where it binds to two different epitopes. In some embodiments the binding member is bispecific in that it binds specifically to TNF alpha, and in addition also to a further target. In some embodiments the binding member is multispecific, that is, it binds specifically to TNF alpha, and in addition also to more than one a further target. The binding member is in some embodiments a monovalent binding member against TNF alpha. The binding member binds to TNF alpha in an immunoglobulin-like manner. In some embodiments the binding member is an immunoglobulin or a fragment thereof. The binding member specifically directed against TNF alpha is generally defined by a single molecule. Such a molecule is typically proteinaceous. The binding member may have one, two or more chains. Where a plurality of chains is included in the binding member, two or more such chains may be covalently or non-covalently coupled to one another.

The binding member, such as the monovalent binding member, inhibits the biological effect of soluble human TNF alpha with an $IC_{50}$ of lower than 50 pM. In some embodiments the $IC_{50}$ is lower than about 40 pM. The $IC_{50}$ has in some embodiments a value of about 30 pM or less.

In some embodiments the monovalent binding member is an antibody fragment. A respective antibody fragment generally has a molecular weight of about 60 kDa or lower. In some embodiments the antibody fragment has a molecular weight of about 55 kDa or less. The molecular weight of the antibody fragment is in some embodiments about 50 kDa or less. In some embodiments the antibody fragment has a molecular weight of about 45 kDa or less. In some embodiments the molecular weight is about 40 kDa or about 35 kDa or less. The molecular weight of the antibody fragment is in some embodiments about 30 kDa or 25 kDa. In some embodiments the antibody fragment has a molecular weight of less than 30 kDa, or less than 25 kDa. The molecular weight of the antibody fragment is in some embodiments about 23 kDa or less, or about 24 kDa or less. In some embodiments the antibody fragment has a molecular weight of about 25 kDa or less, or about 26 kDa or less. The molecular weight of the antibody fragment is in some embodiments 27 kDa or less.

In one aspect, there is provided a binding member directed against TNF alpha. The binding specificity of the binding member may be verified using techniques well known in the art. A plurality of conventional display technologies is available to measure the binding characteristics of a binding member such as an immunoglobulin, immunoglobulin fragment or proteinaceous binding molecule. Li et al. (*Organic & Biomolecular Chemistry* (2006), 4, 3420-3426) have for example demonstrated how a single-chain Fv fragment capable of forming a complex with a selected DNA adapter can be obtained using phage display. Display techniques for instance allow the generation of engineered immunoglobulins and ligands with high affinities for a selected target molecule. It is thus also possible to display an array of peptides or proteins that differ only slightly, typically by way of genetic engineering. Thereby it is possible to screen and subsequently evolve proteins or peptides in terms of properties of interaction and biophysical parameters. Iterative rounds of mutation and selection can be applied on an in vitro basis.

In vitro display technology for the selection of peptides and proteins relies on a physical linkage between the peptide or protein and a nucleic acid encoding the same. A large panel of techniques has been established for this purpose, with the most commonly used being phage/virus display, ribosome display, cell-surface display, 'peptides on plasmids', mRNA display, DNA display, and in vitro compartmentalisation including micro-bead display (for reviews see e.g. Rothe, A., et al., *FASEB J.* (2006) 20, 1599-1610; Sergeeva, A., et al., *Advanced Drug Delivery Reviews* (2006) 58, 1622-1654).

Different means of physically linking a peptide, including a protein, and a nucleic acid are also available. Expression in a cell with a cell surface molecule, expression as a fusion polypeptide with a viral/phage coat protein, a stabilised in vitro complex of an RNA molecule, the ribosome and the respective polypeptide, covalent coupling in vitro via a puromycin molecule or via micro-beads are examples of ways of linking the protein/peptide and the nucleic acid presently used in the art. A further display technique relies on a water-in-oil emulsion. The water droplets serve as compartments in each of which a single gene is transcribed and translated (Tawfik, D. S., & Griffiths, A. D., *Nature Biotech.* (1998) 16, 652-656, US patent application 2007/0105117). This physical linkage between the peptide including the protein, and the nucleic acid (encoding it) provides the possibility of recovering the nucleic acid encoding the selected peptide/protein. Compared to techniques such as immunoprecipitation, in display techniques thus not only binding partners of a selected target molecule can be identified or selected, but the nucleic acid of this binding partner can be recovered and used for further processing. Present display techniques thus provide means for e.g. target discovery, lead discovery and lead optimisation. Vast libraries of peptides or proteins, e.g. antibodies, potentially can be screened on a large scale.

TNF alpha, to which the binding member specifically binds, is a cytokine, which is inter alia involved in the regulation of immune cells. TNF alpha is involved in disorders related to the immune system of an organism, including autoimmune disorders and immune-mediated disorders. TNF alpha is in some embodiments human TNF alpha, which exists as a soluble form and as a membrane form. The membrane form has an intracellular domain, a transmembrane domain and an extracellular domain. The soluble form corresponds to amino acid positions 77 to 233 of the 233 amino acids of the membrane form. The membrane form of human TNF alpha has Uniprot/Swissprot accession number P01375 (version 202 of 4 Mar. 2015).

TNF alpha from other species likewise exists in the form of a soluble molecule and a transmembrane protein. For example canine TNF alpha has a length of 233 amino acids, of which the extracellular domain spans from amino acids 57 to 233. The soluble form spans amino acid positions 77 to 233 (cf. Uniprot/Swissprot accession number P51742, version 112 of 4 Mar. 2015. In some embodiments TNF alpha, to which the binding member specifically binds, is murine TNF alpha, which has Uniprot/Swissprot accession number P06804 (version 167 of 4 Mar. 2015). In some embodiments TNF alpha, to which the binding member specifically binds, is feline TNF alpha, which has Uniprot/Swissprot accession number P19101 (version 110 of 7 Jan. 2015). TNF alpha, to which the binding member specifically binds, is in some embodiments bovine TNF alpha, which has Uniprot/Swissprot accession number Q06599 (version 129 of 4 Mar. 2015). In some embodiments the TNF alpha is Guinea pig TNF alpha, which has Uniprot/Swissprot accession number P51435 (version 106 of 4 Mar. 2015). The TNF alpha is in some embodiments dog TNF alpha, which has Uniprot/Swissprot accession number P51742 (version 112 of 4 Mar. 2015). In some embodiments TNF alpha, to which the binding member specifically binds, is rhesus macaque TNF alpha, which has Uniprot/Swissprot accession number P48094 (version 108 of 4 Mar. 2015).

The binding member disclosed herein may include at least one of the VH CDR sequences CDR-H1, CDR-H2 and CDR-H3 as set forth in SEQ ID Nos.: 6, 7 and 8, respectively, or variants thereof. In some embodiments the binding member includes more than one of the VH CDR sequences CDR-H1, CDR-H2 and CDR-H3, as set forth in SEQ ID Nos.: 6, 7 and 8, respectively, or variants thereof. In some embodiments the binding member includes all of the VH CDR sequences CDR-H1, CDR-H2 and CDR-H3, as set forth in SEQ ID Nos.: 6, 7 and 8, respectively, or variants thereof. The binding member may also include at least one of the VL CDR sequences CDR-L1, CDR-L2 and CDR-L3 as set forth in SEQ ID Nos.: 3, 4 and 5, respectively, or variants thereof. In some embodiments the binding member includes more than one of the VL CDR sequences CDR-L1, CDR-L2 and CDR-L3 as set forth in SEQ ID Nos.: 3, 4 and 5, respectively, or variants thereof. In some embodiments the binding member includes all of the VL CDR sequences CDR-L1, CDR-L2 and CDR-L3 as set forth in SEQ ID Nos.: 3, 4 and 5, respectively, or variants thereof.

In some embodiments the binding member includes at least one of the VH CDR sequences CDR-H1, CDR-H2 and CDR-H3 as set forth in SEQ ID Nos.: 6, 7 and 8, respectively, or variants thereof, but none of the VL CDR sequences CDR-L1, CDR-L2 and CDR-L3 as set forth in SEQ ID Nos.: 3, 4 and 5, respectively, or variants thereof. In some embodiments the binding member includes at least one of the VH CDR sequences CDR-H1, CDR-H2 and CDR-H3 as set forth in SEQ ID Nos.: 6, 7 and 8, respectively, or variants thereof, and at least one of the VL CDR sequences CDR-L1, CDR-L2 and CDR-L3 as set forth in SEQ ID Nos.: 3, 4 and 5, respectively, or variants thereof. In some embodiments the binding member includes at all of the VH CDR sequences CDR-H1, CDR-H2 and CDR-H3 as set forth in SEQ ID Nos.: 6, 7 and 8, respectively, or variants thereof, and at least one of the VL CDR sequences CDR-L1, CDR-L2 and CDR-L3 as set forth in SEQ ID Nos.: 3, 4 and 5, respectively, or variants thereof. In some embodiments the binding member includes at least one of the VH CDR sequences CDR-H1, CDR-H2 and CDR-H3 as set forth in SEQ ID Nos.: 6, 7 and 8, respectively, or variants thereof, and all of the VL CDR sequences CDR-L1, CDR-L2 and CDR-L3 as set forth in SEQ ID Nos.: 3, 4 and 5, respectively, or variants thereof. In some embodiments the binding member includes all of the VH CDR sequences CDR-H1, CDR-H2 and CDR-H3 as set forth in SEQ ID Nos.: 6, 7 and 8, respectively, or variants thereof, and all of the VL CDR sequences CDR-L1, CDR-L2 and CDR-L3 as set forth in SEQ ID Nos.: 3, 4 and 5, respectively, or variants thereof.

Such a binding member is capable of neutralizing soluble human TNF alpha with an $IC_{50}$ of lower than 50 pM. In some embodiments the binding member is capable of neutralizing soluble human TNF alpha with an $IC_{50}$ of lower than about 40 pM. In some embodiments the binding member is capable of neutralizing soluble human TNF alpha with an $IC_{50}$ of lower than about 30 pM or less.

The $IC_{50}$ can, e.g., be determined using a cell based potency assay. In some embodiments, the $IC_{50}$ value above is determined by inhibiting the TNF alpha induced cytotoxicity in PK-15 cells in presence of 1.4 pM rhTNF alpha. In typical embodiments, about 10,000 cells are used and the binding member is titrated at 37° C. The cells are typically incubated with the mixture of binding member and soluble TNF alpha for 12 to 16 hours, in some embodiments for 16 hours. Preferably, the $IC_{50}$ value is the mean value obtained of at least three independent repetitions of such assay. In one embodiment, such assay is the PK-15 assay described in Example 3.

The binding member may also be capable of neutralizing transmembrane (tm) human TNF alpha with an $IC_{50}$ of lower than about 100 nM. In some embodiments this $IC_{50}$ may be lower than about 80 nM or than about 75 nM. In some embodiments the binding member may be capable of neutralizing tm human TNF alpha with an $IC_{50}$ of lower than about 70 nM. The binding member may also be capable of neutralizing tm human TNF alpha with an $IC_{50}$ of lower than about 65 nM or than about 60 nM. In some embodiments the $IC_{50}$ may be lower than about 50 nM. In some embodiments the binding member may be capable of neutralizing tm human TNF alpha with an $IC_{50}$ of lower than about 10 nM.

The $IC_{50}$ for tmTNF alpha may e.g. be measured in an assay using HEK-Dual TNF alpha sensitive cells stimulated with tmTNF alpha expressing CHO cells. For example, such assay is described in detail in example 3. In a typical example, 10,000 CHO cells/well that have been pre-incubated with the binding member and 20,000 HEK-Dual TNF alpha sensitive cells/well are used and cultured at 37° C. for 24 hours.

Thus, in some embodiments, a binding member is provided that is capable of neutralizing soluble human TNF alpha to a greater extent than human transmembrane TNF alpha, where the $IC_{50}$ value for soluble human TNF alpha is at least 100 fold better than the $IC_{50}$ value for human transmembrane TNF alpha. Put differently, the $IC_{50}$ value of a respective binding member for soluble human TNF alpha is 100 fold or more lower when compared to the $IC_{50}$ value of the same binding member for human transmembrane TNF alpha. Hence, the binding member is much more effective in neutralizing soluble human TNF alpha than in neutralizing human transmembrane TNF alpha.

The binding member described herein may e.g., be an antibody (such as full-length immunoglobulin) or an antibody fragment, such as a Fab, Fab', F(ab')$_2$, scFv, Fv fragment, nanobody, VHH or minimal recognition unit) or a non-antibody scaffold.

In a typical embodiment the binding member and in particular a monovalent binding member as described above is a scFv. The VH and VL domains can be connected in either orientation, VL-linker-VH or VH-linker-VL, by a flexible linker. In a preferred embodiment, the orientation is VL-linker-VH, i.e. the light chain variable region being at the N-terminal end and the heavy chain variable region being at the C-terminal end of the polypeptide.

The binding member is in some embodiments a humanized binding member. In some embodiments the binding member is a humanized antibody or a humanized antibody fragment.

In some embodiments an antibody and, in particular, an antibody fragment as disclosed herein includes a variable heavy chain region of subtype VH3. In some embodiments an antibody and, in particular, an antibody fragment as disclosed herein includes a variable light chain region of subtype Vkappa1. In some embodiments an antibody and an antibody fragment as disclosed herein includes both a variable heavy chain region of subtype VH3 and a variable light chain region of subtype Vkappa1. In some embodiments an antibody and an antibody fragment as disclosed herein includes only a variable heavy chain region of subtype VH3 but not a variable light chain region of subtype Vkappa1. In some embodiments an antibody and an antibody fragment as disclosed herein includes only a variable light chain region of subtype Vkappa1 but not a variable heavy chain region of subtype VH3.

Also provided are variants of the sequences disclosed herein. In some embodiments the VH sequence is a variant of SEQ ID No.: 2 and has at least 85% sequence identity to SEQ ID No.: 2. In some embodiments the VH sequence is a variant of SEQ ID No.: 2 and has at least 85% sequence identity to SEQ ID No.: 2. In some embodiments the VH sequence is a variant of SEQ ID No.: 2 and has at least 90% sequence identity to SEQ ID No.: 2. In some embodiments the VH sequence is a variant of SEQ ID No.: 2 and has at least 91% sequence identity to SEQ ID No.: 2. In some embodiments the VH sequence is a variant of SEQ ID No.: 2 and has at least 92% or 93% sequence identity to SEQ ID No.: 2. In some embodiments a respective variant of SEQ ID No.: 2 has at least 93% or 94% sequence identity to SEQ ID No.: 2. In some embodiments the VH sequence is a variant of SEQ ID No.: 2 and has at least 94%, at least 95%, at least 96%, at least 97%, at least 98% or at least 99% sequence identity to SEQ ID No.: 2. In some embodiments the VH sequence is a variant of SEQ ID No.: 2 and has 100% sequence identity to SEQ ID No.: 2.

Additionally or alternatively, the binding member disclosed herein is an antibody that includes a variant of the VL sequence of SEQ ID No.: 1 having at least 85% sequence identity to the sequence of SEQ ID No.: 1. In some embodiments the antibody or variant includes a variable light chain that includes a sequence that has at least 90% sequence identity to SEQ ID No.: 1. In some embodiments the antibody or variant includes a variable light chain that essentially consists of a sequence that has at least 90% sequence identity to SEQ ID No.: 1. In some embodiments the antibody or variant includes a variable light chain that consists of a sequence that has at least 90% sequence identity to SEQ ID No.: 1. In some embodiments the binding member is an antibody including a variant of the VL sequence of SEQ ID No.: 1 having 91% or more, including 92% or more sequence identity to SEQ ID No.: 1. The binding member is in some embodiments an antibody that contains a variant of the VL sequence of SEQ ID No.: 1 with a sequence that has 93% or more, including 94% or more sequence identity to the sequence of SEQ ID No.: 1. In some embodiments the binding member is an antibody that contains a variant of the VL sequence of SEQ ID No.: 1 that has 95% or more, including 96% or more sequence identity to SEQ ID No.: 1. In some embodiments the VL sequence is a variant of SEQ ID No.: 1 and has at least 97% sequence identity to SEQ ID No.: 1. In some embodiments the VL sequence is a variant of SEQ ID No.: 1 and has 97% or more, including 98% or more sequence identity to SEQ ID No.: 1. The binding member is in some embodiments an antibody that includes a variant of the VL sequence of SEQ ID No.: 1 having at least 99% sequence identity to the sequence of SEQ ID No.: 1. In some embodiments the VL sequence is a variant of SEQ ID No.: 1 and has 100% sequence identity to SEQ ID No.: 1.

In one embodiment, such antibody includes a VH sequence having 85% or more, such as 90%, 91%, 92%, 93%, 94%, 95%, 96%, 97%, 98%, 99% or more and preferably 100% sequence similarity to SEQ ID No.: 2. Additionally or alternatively, the antibody includes a VL sequence that has 85% or more, such as 90%, 91%, 92%, 93%, 94%, 95%, 96%, 97%, 98%, 99% or more, and preferably 100% sequence similarity to SEQ ID No.: 1.

In a preferred embodiment, the antibody includes the VH as set forth in to SEQ ID No.: 1 and the VL as set forth in SEQ ID No.: 2 or variants thereof. The framework sequences of SEQ ID Nos.: 1 and 2 are derived from a human immunoglobulin described in WO 03/097697 A (ESBATech AG). Its VH and VL framework sequences have been modified for humanization and stabilization of rabbit antibodies, see, e.g., WO 2009/155726 A (ESBATech, AN ALCON BIOMEDICAL RESEARCH UNIT LLC) ; BORRAS, L., et al. Generic approach for the generation of stable humanized single-chain Fv fragments from rabbit monoclonal antibodies. *JBC* 2010, vol. 285, no. 12, p. 9054-9066. Variants of SEQ ID Nos.: 1, 2, 11 or 12 should remain stable in a scFv format, i.e. they remain monomeric to a high degree after prolonged incubation. For example, "remain monomeric to a high degree after prolonged incubation" as used herein refers, e.g., to a monomer content of at least 80% at 10mg/mL in PBS pH 7.2 (phosphate buffered saline) at 4° C., 22° C. or 37° C. after 2 weeks of incubation.

The binding member, in particular in case of a scFv, may include a linker sequence. Such linker sequence has typically ten to about 25 amino acids. Usually, such linker peptide is rich in glycines, which confer flexibility, as well as serines and/or threonines for improved solubility. In a preferred embodiment, a $(GGGGS)_4$ linker (SEQ ID No.: 10) or a variant thereof is used. Variations of this motif having three to five repeats may also be used. Further suitable linkers are described, e.g., in ALFTHAN, K. Properties of a single-chain antibody containing different linker peptides. *Prot Eng* 1995, vol. 8, no. 7, p. 725-731.

Thus, in some embodiments, the binding member has an amino acid sequence that includes SEQ ID No 9. In some embodiments the binding member has an amino acid sequence that essentially consists of SEQ ID No 9. In one embodiment, the binding member has an amino acid sequence that consists of SEQ ID No 9.

In certain embodiments variants of the binding member provided herein are contemplated. For example, it may be desirable to improve antigen binding, antibody-dependent cell-mediated cytotoxicity (ADCC), complement-dependent cytotoxicity (CDC), to reduce susceptibility to proteolysis and/or susceptibility to oxidation, to increase stability or solubility, to decrease immunogenicity and/or to alter other biological, biochemical or biophysical properties of the binding member. In some embodiments the variant does not show any improvement over the parent binding member. A variant may in some embodiments be a proteinaceous molecule that differs from a given binding member in one, two or more positions of its amino acid sequence. Typically the difference from a given binding member is a substitution. In some embodiments the difference from a given binding member is a deletion. A variant may be a mutein, i.e. a peptide/protein obtained from the expression of a gene sequence altered by sitespecific mutagenesis.

Variants of the binding members provided herein may be prepared by protein and/or chemical engineering, introducing appropriate modifications into the nucleic acid sequence encoding the binding member, or by protein/peptide synthesis. A variant may be obtained by any combination(s) of one or more deletions, substitutions, additions and insertions to the framework or to the CDRs, provided that the generated binding member possesses the desired characteristics for which it can be screened using appropriate methods. In some embodiments a variant of a binding member differs from a particular sequence of a binding member defined herein by one or two substitutions. In some embodiments a variant of a binding member differs from a particular sequence of a binding member defined herein by up to five substitutions. A substitution in an amino acid sequence of a binding member may be a conservative substitution as described above. Examples of conservative substitutions include:

1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glutamic acid (E) by aspartic acid (D);
7. Substituting glycine (G) by alanine (A);
8. Substituting histidine (H) by arginine (R) or lysine (K);
9. Substituting isoleucine (I) by leucine (L);
10. Substituting methionine (M) by leucine (L);
11. Substituting phenylalanine (F) by tyrosine (Y);
12. Substituting proline (P) by alanine (A);
13. Substituting serine (S) by threonine (T);
14. Substituting tryptophan (W) by tyrosine (Y);
15. Substituting phenylalanine (F) by tryptophan (W); and/or
16. Substituting valine (V) by leucine (L) and vice versa.

The sequences described herein may include one or more, such as two or three of such conservative substitutions. In some embodiments a binding member disclosed herein includes a sequence that has four or more conservative substitutions in comparison to a sequence disclosed herein. In some embodiments a binding member includes a sequence that has five or more conservative substitutions. In some embodiments a binding member contains six or more, such as seven or more conservative substitutions relative to a sequence disclosed herein. In some embodiments a binding member may include eight, nine, ten, eleven, twelve or more of such conservative substitutions.

Non-conservative substitutions may lead to more substantial changes, e.g., with respect to the charge, dipole moment, size, hydrophilicity, hydrophobicity or conformation of the polypeptide. In one embodiment the binding member includes one or more, such as two, three, four, five, six, seven, eight, nine, ten, eleven, twelve or more of such non-conservative substitutions.

Modifications may be present in the CDRs or in the framework sequences. For example, the CDRs provided herein may include one, two, three, four, five or even more modifications. For example, the CDR-L1, CDR-L2 and CDR-L3 sequences taken as a whole are 75% or more, such as 76% or more, 77% or more, 78% or more, 79% or more, 80% or more, 85% or more, 90% or more, 91% or more, 92% or more, 93% or more, 94% or more, 95% or more, 96% or more, 97% or more, 98% or more, and preferably 99% or more identical to the CDRs provided herein, in particular to (i) SEQ ID Nos.: 3, 4, and 5. Additionally or alternatively, the CDR-H1, CDR-H2 and CDR-H3 sequences taken as a whole are at least 80%, such as at least 81%, 82%, 83%, 84%, 95%, 90%, 91%, 92%, 93%, 94%, 95%, 96%, 97%, 98% or preferably 99% identical to the CDRs provided herein, in particular to (i) SEQ ID Nos.: 6, 7 and 8.

In one embodiment the CDR-L1, CDR-L2, CDR-L3, CDR-H1, CDR-H2 and CDR-H3 taken as a whole are at least 85%, such as 90%, 91%, 92%, 93%, 94%, 95%, 96%, 97%, 98% or preferably 99% similar to the CDRs provided herein. Additionally or alternatively, the CDR-L1, CDR-L2, CDR-L3, CDR-H1, CDR-H2 and CDR-H3 taken as a whole are at least 85%, such as 90%, 91%, 92%, 93%, 94%, 95%, 96%, 97%, 98% or preferably 99% similar to the CDRs provided herein.

Additionally or alternatively, a variant may include one or two, substitutions in any one of sequence SEQ ID No.: 1 to 10. In some embodiments a variant includes three substitutions in any one of sequence SEQ ID No.: 1 to 10. In some embodiments a variant includes four substitutions in any one of sequence SEQ ID No.: 1 to 10.

A preferred type of variant is one where one or more entire CDRs are replaced. Typically, the CDR-H3 and CDR-L3 contribute most significantly to antigen binding. For example, the entire CDR-L1, CDR-L2, CDR-H1 and/or CDR-H2 may be replaced by a different CDR of natural or artificial origin. In some embodiments, one or more CDRs are replaced by an alanine-cassette.

Additionally or alternatively, the VH of the antibody may include one or more solubility enhancing point mutations. WO2009/155725 (ESBATech, a Novartis Company) describes a motif, which has proven to increase the overall solubility of the antibody. The residues are placed at positions located in the interface of the variable domain and the constant domain of an antibody and stabilize in particular antibody fragments such as scFv, lacking the constant domain. In particular, one or two of the following residues are present:

(i) serine (S) at heavy chain amino acid position 12 (according to AHo numbering);
(ii) serine (S) or threonine (T) at heavy chain amino acid position 103 (according to AHo numbering); and/or
(iii) serine (S) or threonine (T) at heavy chain amino acid position 144 (according to AHo numbering).

In some embodiments all three of these residues are present.

In some embodiments the antibody has a serine at VH position 12; a serine at VH position 103; and a threonine at VH position 144 (all AHo numbering).

In some embodiments, a variant of a binding member as disclosed herein retains, when compared to the binding member, specific binding to TNF alpha. The variant may for example retain specific binding to human TNF alpha. In some embodiments, a variant binding member as disclosed herein has a potency ($IC_{50}$) with regard to inhibiting the biological effect of soluble human TNF alpha of lower than about 500 pM. In some embodiments the potency of the variant with regard to inhibiting the biological effect of soluble human TNF alpha is lower than about 400 pM. The $IC_{50}$ of the variant, when compared to the binding member, may in some embodiments be lower than about 300 pM, including about 200 pM, about 100 pM, or about 50 pM. In one embodiment a variant of a binding member has a potency ($IC_{50}$) with regard to inhibiting the biological effect of soluble human TNF alpha of lower than about 40 pM, relative to the binding member.

A variant of a binding member is in some embodiments capable of inhibiting transmembrane TNF alpha with a potency ($IC_{50}$) of lower than about 100 nM, preferably of about 80 nM or lower. In some embodiments a variant is capable of inhibiting transmembrane TNF alpha with a potency ($IC_{50}$) of about 75 nM or lower. In some embodiments a variant is capable of inhibiting transmembrane TNF alpha with a potency ($IC_{50}$) of about 70 nM or lower, such as about 65 nM or lower. In some embodiments a variant is capable of inhibiting transmembrane TNF alpha with a potency ($IC_{50}$) of about 60 nM or lower.

A variant of a binding member is in some embodiments cross-reactive with human and non-human TNF alpha. A variant of a binding member is in some embodiments capable of binding to the same TNF alpha species as the (parent) binding member binds to, e.g., cynomolgus monkey, canine, feline and/or rhesus macaque TNF alpha. In some embodiments a variant of a binding member competes with the binding member disclosed herein for binding to TNF alpha. A variant may for instance compete with the binding member disclosed herein for binding to human TNF alpha. In some embodiments the variant is capable of competing with the binding member disclosed herein for binding to the same non-human TNF alpha to which the binding member is capable to bind.

In some embodiments, a variant binding member as disclosed herein retains specific binding to TNF alpha; has a potency ($IC_{50}$) with regard to inhibiting the biological effect of soluble human TNF alpha of lower than about 500 pM, such as lower than 400 pM, 300pM, 200 pM, 100 pM, 50 pM, preferably of lower than 40 pM; inhibits transmembrane TNF alpha with a potency $IC_{50}$ of lower than 100 nM, preferably of lower than about 80 nM, 75 nM, 70 nM, 65 nM or 60 nM; is cross-reactive with human and non-human TNF alpha and binds to the same TNF alpha species as the parent binding member binds to, e.g., cynomolgus monkey, canine, feline and/or rhesus macaque TNF alpha; and competes with the binding member disclosed herein for binding to TNF alpha, such as human TNF alpha and preferably to the same non-human TNF alpha to which the binding members binds.

Variants may also be prepared by chain shuffling of light and heavy chains. A single light chain can be combined with a library of heavy chains to yield a library of variants. In one embodiment, the single light chain is selected from the group of VL sequences recited above and/or the library of heavy chains includes one or more of the VH sequences recited above. Likewise, a single heavy chain can be combined with a library of light chains. In some embodiments, the single heavy chain is selected from the group of VH sequences recited above and/or the library of light chains includes one or more of the VL sequences recited above.

A binding member can include any of the VL and/or the VH sequences mentioned above. Binding members having a single domain format, such as a nanobody or a VHH, include only one of either the VL or VH sequences mentioned above, preferably the VH sequence and are monovalent. Multivalent binding members, such as F(ab')$_2$ fragments, bis-scFv (also known as tandem scFv) or diabodies, in particular bispecific binding members, may include one or more of the VL sequences mentioned above and/or one or more of the VH sequences mentioned above. Multivalent binding members may include VH and/or VL sequences targeting antigens different to TNF alpha.

The binding members disclosed herein are particularly stable. In particular the monovalent antibody fragments disclosed herein and the scFvs disclosed herein are particularly stable. As used herein the term "stability" refers to the biophysical property of the polypeptide to remain monomeric in solution after prolonged incubation and/or incubation at elevated temperature. Unstable polypeptides tend to dimerize or oligomerize and even precipitate, thereby decreasing shelf-life and becoming less suitable for pharmaceutical applications.

The binding members provided herein and in particular the monovalent antibody fragment above remain monomeric at least to 75%, preferably at least to 80%, 85%, 90%, 95% and most preferably to 97% after being incubated for 1 week at 37° C. at a concentration of 10 mg/mL in PBS at pH 7.2. Additionally or alternatively, the binding member provided herein and in particular the monovalent antibody fragment above remains monomeric to 90% or more after 1 week at 4° C. or at 22° C. at a concentration of 10 mg/mL in PBS at pH 7.2. In some embodiments the binding member disclosed herein remains monomeric to 92% or more, such as 94% or more after 1 week at 4° C. or at 22° C. at a concentration of 10 mg/mL in PBS at pH 7.2. In some embodiments the binding member remains monomeric to 95% or more, such as 96% or more, or 97% or more after 1 week at 4° C. or at 22° C. at a concentration of 10 mg/mL in PBS at pH 7.2. In one embodiment the binding member remains monomeric to 99% or more after 1 week at 4° C. or at 22° C. at a concentration of 10 mg/mL in PBS at pH 7.2.

The fraction of monomers can, e.g., be determined by SE-HPLC (Size Exclusion-High-Performance Liquid Chromatography). A suitable mobile phase for such testing is, e.g., PBS pH 7.2. The monomer content can be quantified by peak integration of the UV280 signal measured during the protein chromatography. A suitable system is, e.g., a Dionex UltiMate 3000 RS HPLC controlled by Chromeleon® 6.5 software that also allows for subsequent chromatogram analysis and peak quantification.

The binding member, such as a monovalent antibody fragment, including a scFv, may have a theoretical isoelectric point (pI) in the range of 5 to 10, preferably 7 to 9. The theoretical pI can, for example, be calculated by using the ProtParam tool on the ExPASy Server (available at http://web.expasy.org/protparam/; see also GASTEIGER E. et al. Protein Identification and Analysis Tools on the ExPASy Server. (In) The Proteomics Protocols Handbook. Edited by WALKER J. M. Totowa: Humana Press Inc., 2005. ISBN 9781588295934. p. 571-607).

The binding member, e.g. the scFv, can be concentrated in PBS pH 7.2 to concentrations higher than 35 mg/ml, preferably higher than 40 mg/ml, 45 mg/ml, 47 mg/ml, 48 mg/ml, 49 mg/ml, most preferably higher than 50 mg/ml. The higher the binding member can be concentrated, the higher the solubility of the binding member.

The binding member can be cross-reactive with TNF alpha from non-human species, such as, without being limited to, feline TNF alpha, rhesus macaque TNF alpha, canine TNF alpha. This is particularly useful for preclinical testing purposes, e.g., animal studies. Preferably, the binding member is not cross-reactive with human lymphotoxin alpha2/beta1, human lymphotoxin alpha1/beta2, human CD40 Ligand/TNFSF5 and/or humanTNF beta/TNFSF1.

Provided is also a binding member competing with an antibody as disclosed herein, the binding member being for binding to human TNF alpha. For example, such competing (or cross-blocking) binding member may be neutralizing. In typical embodiments such a binding member has a potency $IC_{50}$ of lower than 50 pM when inhibiting soluble 1.4 pM rhTNF alpha induced cytotoxicity in PK-15 cells.

As used herein, the term "competing" refers to the competition between binding members for binding to the same target. Competition can be determined by competitive binding assays in which the binding member of interest prevents or inhibits or reduces specific binding of the binding members disclosed herein to a common antigen (here, hTNF alpha or a fragment thereof). Such competitive binding assays are known in the art and include, without being limited to, solid phase direct or indirect radioimmunoassay (RIA) and solid phase direct or indirect enzyme immunoassay (EIA). Typically, such assay involves the use of purified antigen bound to a solid surface, a binding member to be tested and the reference binding member as described herein. Competitive inhibition is measured by determining the amount of either (i) the reference binding member bound to the solid surface in the presence of the binding member to be tested, or (ii) the binding member to be tested bound to the solid surface in the presence of the reference binding member. A competing binding member may bind (i) to the same epitope as the reference binding member, (ii) to an overlapping epitope, or (iii) to a different epitope on the same target molecule but sterically hindering binding of the reference binding member to its target.

Usually, when a competing binding member is present in excess, it will reduce specific binding of the binding member as described herein to TNF alpha, i.e. it cross-blocks binding, by 40-45% or more. When present in excess, a competing binding member will in some embodiments reduce specific binding of the binding member to TNF alpha by 45-50% or more, such as 50-55% or more, or 55-60% or more. In some embodiments binding of a binding member in presence of the competing binding member is reduced by 60-65% or more, 65-70% or more, 70-75% or more, or 75% or more. Preferably, binding of a binding member described herein in presence of the competing binding member is reduced by 80-85% or more. In some embodiments binding of a binding member in presence of the competing binding member is reduced by 85-90% or more, including 90-95% or more. In some embodiments binding of a binding member in presence of the competing binding member is reduced by 95-97% or more. In some embodiments binding of a binding member in presence of the competing binding member is reduced by 97% or more.

In some embodiments, the competing binding member binds to hTNF alpha with an affinity $K_D$ of about 1 pM or more. In some embodiments, the competing binding member binds to hTNF alpha with a $K_D$ of about 10 pM or more. In some embodiments, the competing binding member binds to hTNF alpha with an affinity $K_D$ of about 100 pM or more, such as 500 pM or more. The competing binding member binds in some embodiments to hTNF alpha with a $K_D$ of about 1 nM or more. In some embodiments, the competing binding member binds to hTNF alpha with a $K_D$ of about 10 nM or more.

Thus, in one aspect, a binding member is provided, that
(i) is capable of binding soluble and transmembrane TNF alpha;
(ii) neutralizes soluble TNF alpha with an $IC_{50}$ of about 30±6 pM as measured by inhibiting 1.4 pM rhTNF alpha induced cytotoxicity in PK-15 cells;
(iii) neutralizes tmTNF alpha with an $IC_{50}$ of about 50 nM when measured in a HEK-Dual TNF alpha sensitive cells stimulated with tm expressing CHO cells; and/or
(iv) is cross-reactive with soluble human, rhesus macaque, cynomolgus monkey, canine and feline TNF alpha. In one embodiment, the binding member includes at least one, such as at least CDR-L3 and CDR-H3, preferably all CDRs as set forth in SEQ ID Nos. 3-8. In one embodiment, the binding member is a scFv that includes SEQ ID No.: 9 and has further one or more features of
(v) being stable to at least 90% at 4° C. and a concentration 10 mg/mL in PBS pH 7.2 for 6 months;

(vi) being stable to at least 95% at 4° C. and a concentration of 10 mg/mL in PBS pH 7.2 for 2 weeks;
(vii) having a Tm of 76° C.; and/or
(viii) having a pI of 8.27.

In one embodiment, the binding member disclosed herein is monovalent, such as a scFv or a Fab fragment. In another embodiment, the binding member is multivalent. Such multivalent molecule can be bivalent (such as a full-length immunoglobulin or a F(ab')₂ fragment) or includes at least three target binding sites.

The multivalent binding member can be a bispecific antibody such as a diabody, a single-chain diabody or a tandem scFv (see, e.g., KONTERMANN, R. E. Methods in Molecular Biology. Edited by LO, B. Totowa, N.J.: Humana Press, 2004. ISBN 1588290921. p. 227-242). A respective bispecific antibody may well use shorter linkers than those described above for scFv, i.e., having only one to three repeats of the basic motif of SEQ ID NO: 14 (see, e.g., HOLLIGER, P., et al. Diabodies: small bivalent and bispecific antibody fragments. *PNAS* 1993, vol. 90, no. 14, p. 6444-6448). In another embodiment the multivalent binding member is a triabody, a minibody or tetrabody.

Provided are also T-bodies that include an antibody as disclosed herein. T-bodies are immunoglobulin T-cell receptors (cIgTCRs) which combine the antigen recognition of antibodies with the signal and effector properties of the T-cell receptor complex. In such constructs the antibody is in some embodiments an antibody fragment such as a Fv, a Fab, a scFv or a scFv-Fc. In one embodiment the antibody is a scFv. For further discussion of the general design of T-bodies and their applications, see, e.g., SCHIRRMANN, T. and Pecher, G. Handbook of Therapeutic Antibodies. Edited by DÜBEL, S. Weinheim: Wiley-VCH, 2009. ISBN 3527314539. p.533-561.

A binding member according to the present disclosure may in some embodiments include a capture moiety such as a streptavidin binding tag, e.g. the STREP-TAGS® described in US patent application US 2003/0083474, U.S. Pat. No. 5,506,121 or U.S. Pat. No. 6,103,493. Further examples of a capture moiety include, but are not limited to, maltose-binding protein, glutathione-S-transferase (GST), calmodulin binding peptide (CBP), FLAG-peptide (e.g. of the sequence Asp-Tyr-Lys-Asp-Asp-Asp-Asp-Lys-Gly), the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the Vesicular Stomatitis Virus Glycoprotein (VSV-G) epitope of the sequence Tyr-Thr-Asp-Ile-Glu-Met-Asn-Arg-Leu-Gly-Lys, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu.

A further example of a capture moiety is a metal chelator, which is capable of binding a metal ion. A respective capture moiety may be ethylenediamine, ethylenediaminetetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (dimmercaprol), porphine or heme.

In line with the standard method of immobilised metal affinity chromatography used in the art, for example an oligohistidine tag is capable of forming a complex with copper ($Cu^{2+}$), nickel ($Ni^{2+}$), cobalt ($Co^{2+}$), or zink ($Zn^{2+}$) ions, which can for instance be presented for chromatography purposes by means of the chelator nitrilotriacetic acid (NTA).

Nucleic Acids, Vectors, Host Cells and Method of Production

A binding member as described herein may be encoded by a single nucleic acid sequence or by a plurality of nucleic acid sequences. In the case of a plurality of nucleic acid sequences each sequence may encode one variable region. In some embodiments a nucleic acid sequence may encode two or more variable regions. Generally a plurality of nucleic acid sequences encodes the variable regions of a binding member. Typically each variable region is encoded by one distinct nucleic acid sequence. The respective nucleic acid sequences encoding the variable regions may be included in a single nucleic acid molecule. In some embodiments two or more nucleic acid sequences encoding the variable regions are included in a single nucleic acid molecule. In some embodiments each nucleic acid sequence encoding a variable region is included in a single distinct nucleic acid molecule. Accordingly, a plurality of nucleic acid molecules may be used in the production of a binding member, for example each encoding at least one variable region. A respective nucleic acid molecule may in some embodiments define an expression cassette. As indicated above, an expression cassette is a nucleic acid molecule capable of directing expression of a particular nucleotide sequence in an appropriate host cell.

An expression cassette includes a promoter operatively linked to the nucleotide sequence of interest, which is operatively linked to one or more termination signals. It may also include sequences required for proper translation of the nucleotide sequence. The coding region can encode a polypeptide of interest and can also encode a functional RNA of interest, including but not limited to, antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, however, the expression cassette is heterologous with respect to the host; i.e., the particular nucleic acid sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant or an animal, the promoter can also be specific to a particular tissue, organ, or stage of development.

Knowing the sequence of the binding member or of its parts, cDNAs encoding the polypeptide sequence can be generated by methods well known in the art, e.g. by gene synthesis. These cDNAs can be cloned by standard cloning and mutagenesis techniques into a suitable vector such as an expression vector or a cloning vector. Optionally, the variable light chain is encoded by a separate nucleic acid than the variable heavy chain of the antibody. Further, additional sequences such as a tag (e.g., a His-tag), a constant domain for the production of a Fab or a full-length immunoglobulin, a linker, the coding sequence of a second binding specificity or another functional polypeptide such as an enzyme to generate a fusion construct or a bispecific molecule may be included into the genetic construct.

Based on the cloning strategy chosen, genetic constructs may generate a binding member having one or more additional residues at the N-terminal or C-terminal end. For example, an N-terminal methionine derived from the start codon or an additional alanine may be present in an expressed polypeptide, unless it has been clipped off post-translationally. It is therefore to be understood that the antibodies disclosed herein include the disclosed sequences rather than consist of them. Thus, in one embodiment, the binding member has the sequence of SEQ ID No. 9 or 19.

Basic protocols of standard cloning, mutagenesis and molecular biology techniques are described in, e.g., Molecular Cloning, A Laboratory Manual (GREEN, M. and Sambrook, J. Molecular Cloning: a Laboratory Manual. 4th edition. Cold Spring Harbor Laboratory, 2012. ISBN 1936113422.).

Appropriate host cells for the expression of the genetic constructs can be prokaryotic or eukaryotic. Suitable prokaryotic host cells are gram-negative or gram-positive and include species of the *Escherichia, Erwinina, Enterobacter, Klebsiella, Pseudomonas* or *Bacillus* families. In some embodiments the host cell is *Escherichia coli*, such as one or more of *E. coli* strains BL21 (DE3) (Life Technologies™, cat. no. C6000-03) and Origami™ 2(DE3) (Novagen, cat. no 71345).

If post-translational modifications such as glycosylation or phosphorylation are desired, it may be advantageous to use an eukaryotic host cell. For example, eukaryotic microbes such as commonly used Saccharomyces cerevisiae or Pichia pastoris strains may serve as a host cell. Suitable examples of a host cells also include a plant or an animal cell, in particular insect or mammalian cells. Suitable mammalian cells include, without being limited to, Chinese Hamster Ovary Cells (CHO), Human Embryonic Kidney Cells (HEK), Human Umbilical Vein Endothelial Cells (HUVEC) or NS0 myeloma cells.

The binding member can be produced by way of expression in a suitable host cell. For example, the expression vectors described above are introduced into a host cell by standard techniques such as electroporation or chemical transformation. The transformed cells are then cultivated under conditions adequate for recombinant protein expression, typically in appropriate nutritional media, optionally modified for inducing promotors, selecting transformants, or amplifying encoding sequences of interest. The binding member is recovered from the culture and optionally purified using standard techniques in the art. The yield of recombinant protein may be improved by optimizing media and culture conditions such as temperature or oxygen supply. In prokaryotes the binding member can be produced in the periplasm, intracellularly as inclusion bodies or be secreted into the medium. Upon harvest, the protein can be purified using methods well known in that art such as gel filtration, ion exchange chromatography, reversed phase chromatography, hydrophobic interaction, mixed mode chromatography and/or affinity chromatography.

In one embodiment the binding member is produced in a cell-free system. This typically involves in vitro transcription followed by in vitro translation of nucleic acid product templates encoding a protein as described herein, e.g., plasmid DNA or PCR product templates. For example, crude lysates from growing cells are used, providing the necessary enzymes such as the cellular protein synthesis machinery. The necessary building blocks such as amino acids or nucleobases as well as energy delivering molecules and others can be exogenously supplied. Cell-free expression systems can, for example, be based on lysed rabbit reticulocytes (e.g., Rabbit Reticulocyte Lysate System, Promega, cat. no. L4540), HeLa cells (e.g., 1-Step Human In Vitro Translation Kit, Thermo Scientific, cat. no. 88881), insect cells (e.g., EasyXpress Insect Kit II, Qiagen, cat. no. 32561), wheat germs (e.g., Wheat Germ Extract, Promega, cat. no. L4380), or *E.coli* cells (e.g., PURExpress® In Vitro Protein Synthesis Kit, NEB, cat. no. E6800S). Also, optimized cell-free antibody expression systems for improved disulfide bond generation can be used for production. Commercially available kits include insect cell lysates (e.g., EasyXpress Disulfide Insect Kit, Qiagen, cat. no. 32582) or *E.coli* cell lysates (e.g., EasyXpress Disulfide *E. coli* Kit, Qiagen, cat. no. 32572). Cell-free protein synthesis has, e.g., the advantage of being fast, achieving high product yields, allowing for easy modification of reaction conditions, forming a low degree of or even no byproducts. Cell-free protein synthesis may involve biological and/or chemical steps which cannot be conducted in purely biological or chemical production systems. For example, non-natural or chemically-modified amino acids can be incorporated into the protein at desired positions. ScFv-toxin fusion proteins have been successfully produced in cell-free systems (NICHOLLS, P. J., et al. Characterization of single-chain antibody (sFv)-toxin fusion proteins produced in vitro in rabbit reticulocyte lysate. *JBC* 1993, vol. 268, pp. 5302-5308). Thus, in one embodiment a method of producing the binding member described herein or the T-body above is provided, which includes the steps of (a) providing a cell-free system, (b) providing a nucleic acid product template encoding the binding member above or the T-body above, (c) allowing for transcription and translation of the nucleic acid product template; (d) recovering; and optionally (e) purifying the binding member or the T-body, respectively.

Additionally or alternatively, a method of producing the binding member described herein includes at least one step of chemical synthesis. For example, the method may be entirely chemical. In another embodiment, the cell-based or the cell-free production systems described above include such at least one step of chemical synthesis.

In some embodiments a binding member as described herein is produced in a cell-based system using an expression vector for intracellular expression in *E. coli*. Upon expression the polypeptide is generated as an inclusion body within the host cell which is separated from further cell particles followed by solubilisation in a denaturing agent such as guanidine hydrochloride (GndHC1) and refolded by renaturation procedures well known to the skilled person.

The desired binding member may also be produced in a transgenic animal. A suitable transgenic animal may be obtained according to standard methods, for example including the steps of (i) making the transgenic embryo, e.g. by micro injecting DNA constructs that include the coding sequence of the binding members as well as suitable control sequences into eggs; (ii) transferring the eggs into a pseudopregnant recipient females; (iii) monitoring gestation or pregnancy; and (iv) selecting a descendant expressing the desired antibody.

It is to be understood that the nucleic acids, vectors, host cells and method of production described above also apply to the binding members (insofar as they are a protein) and/or to T-bodies described herein.

Chemical and/or Biological Modifications

In one aspect the binding member disclosed herein is chemically and/or biologically modified. Such modification may include, but is not limited to, glycosylation, PEGylation, HESylation, Albumin fusion technology, PASylation, labelling with dyes and/or radioisotopes, conjugation with enzymes and/or toxins, phosphorylation, hydroxylation and/or sulfation. Likewise, any binding member, the nucleic acid sequence, the vector and/or the host cell described above can be modified accordingly.

Chemical and/or biological modifications may be conducted to optimize pharmacodynamics or water solubility of the protein or to lower its side effects. For example, PEGylation, PASylation and/or HESylation may be applied to slow down renal clearance and thereby increase plasma half-life time of the binding member. Additionally or alternatively, a modification may add a different functionality to the protein, e.g. a toxin to more efficiently combat cancer cells, or a detection molecule for diagnostic purposes.

Glycosylation refers to a process that attaches carbohydrates to proteins. In biological systems, this process is performed enzymatically within the cell as a form of co-translational and/or post-translational modification. A protein, here the binding member such as an antibody, can also be chemically glycosylated. Typically, but not limited to, glycosylation is (i) N-linked to a nitrogen of asparagine or arginine side-chains; (ii) O-linked to the hydroxy oxygen of serine, threonine, tyrosine, hydroxylysine, or hydroxyproline side-chains; (iii) involves the attachment of xylose, fucose, mannose, and N-acetylglucosamine to a phosphoserine; or (iv) in form of C-mannosylation wherein a mannose sugar is added to a tryptophan residue found in a specific recognition sequence. Glycosylation patterns can, e.g., be controlled by choosing appropriate cell lines, culturing media, protein engineering manufacturing modes and process strategies (HOSSLER, P. Optimal and consistent protein glycosylation in mammalian cell culture. *Glycobiology* 2009, vol. 19, no. 9, p. 936-949.).

Protein engineering to control or alter the glycosylation pattern may involve the deletion and/or the addition of one or more glycosylation sites. The creation of glycosylation sites can conveniently be accomplished by introducing the corresponding enzymatic recognition sequence into the amino acid sequence of the binding member or by adding or substituting one or more of the above enumerated amino acid residues.

It may be desirable to PEGylate the binding member. PEGylation may alter the pharmacodynamic and pharmacokinetic properties of a protein. Polyethylene-glycol (PEG) of an appropriate molecular weight is covalently attached to the protein backbone (see, e.g., PASUT, G. and Veronese, F. State of the art in PEGylation: the great versatility achieved after forty years of research. *J Control Release* 2012, vol. 161, no. 2, p. 461-472). PEGylation may additionally reduce the immunogenicity by shielding the PEGylated protein from the immune system and/or alter its pharmacokinetics by, e.g. increasing the in vivo stability of the binding member, protecting it from proteolytic degradation, extending its half-life time and by altering its biodistribution.

Similar effects may be achieved by PEG mimetics, e.g., HESylating or PASylating the antibody. HESylation utilizes hydroxyethyl starch ("HES") derivatives, whereas during PASylation the antibody becomes linked to conformationally disordered polypeptide sequences composed of the amino acids proline, alanine and serine. These PEG mimetics and related compounds are, e.g., described in BINDER, U. and Skerra, A. Half-Life Extension of Therapeutic Proteins via Genetic Fusion to Recombinant PEG Mimetics, in Therapeutic Proteins: Strategies to Modulate Their Plasma Half-Lives. Edited by KONTERMANN, R., Weinheim, Germany: Wiley-VCH, 2012. ISBN: 9783527328499. p. 63-81.

The binding member may include an epitope such as a salvage receptor binding epitope. Such salvage receptor binding epitope typically refers to an epitope of the Fc region of an IgG molecule (e.g., IgG1, IgG2, IgG3, or IgG4) and has the effect of increasing the in vivo half-life of the molecule.

Additionally or alternatively, the binding member is labelled with or conjugated to a second moiety which ascribes ancillary functions following target binding. The second moiety may, e.g., have an additional immunological effector function, be effective in drug targeting or useful for detection, without being limited thereto. The second moiety can, e.g., be chemically linked or fused genetically to the binding member using known methods in the art.

Molecules which may serve as second moiety include, without being limited to, a radionuclide, also called a radioisotope, an apoenzyme, an enzyme, a co-factor, a peptide moiety such as a HIS-tag, a protein, a carbohydrate such as a mannose-6-phosphate tag, a fluorophore such as fluorescein isothiocyanate (FITC), phycoerythrin, a green/blue/red or other fluorescent protein, allophycocyanin (APC), a chromophore, a vitamin such as biotin, a chelator, an antimetabolite such as methotrexate, a liposome, a toxin such as a cytotoxic drug, or a radiotoxin. Illustrative examples of a radionuclide are $^{35}$S, $^{32}$P, $^{14}$C, $^{18}$F, and $^{125}$I. Examples of suitable enzymes include, but are not limited to, alkaline phosphatase, horseradish peroxidase, beta-galactosidase and angiogenin. An illustrative example of a suitable protein is a lectin. Examples of suitable cytotoxic drugs include, but are not limited to, taxol, gramicidin D and colchicine.

A labelled binding member is particularly useful for in vitro and in vivo detection or diagnostic purposes. For example, a binding member labelled with a suitable radioisotope, enzyme, fluorophore or chromophore can be detected by radioimmunoassay (RIA), enzyme-linked immunosorbent assay (ELISA), or flow cytometry-based single cell analysis (e.g., FACS analysis), respectively. Similarly, the nucleic acids and/or vectors disclosed herein can be used for detection or diagnostic purposes, e.g. using labelled fragments thereof as probes in hybridization assays. Labelling protocols may, e.g., be found in JOHNSON, I. and Spence, M. T. Z. Molecular Probes Handbook, A Guide to Fluorescent Probes and Labeling Technologies. Life Technologies, 2010. ISBN: 0982927916.

It is to be understood that the outlined above also applies to T-bodies.

Compositions

A binding member, a nucleic acid sequence and/or a vector as disclosed herein may be provided in a composition which further includes a suitable carrier, excipient or diluent. In typical embodiments a respective composition includes an antibody described herein.

Such composition can, e.g., be a diagnostic, a cosmetic or a pharmaceutical composition. For therapeutic or cosmetic purposes, the composition is a pharmaceutical composition including a pharmaceutical carrier, excipient or diluent, i.e. not being toxic at the dosages and a concentration employed.

Suitable "carrier", "excipients" or "diluents" include, without being limited to: (i) buffers such as phosphate, citrate, or other, organic acids; (ii) antioxidants such as ascorbic acid and tocopherol; (iii) preservatives such as 3-pentanol, hexamethonium chloride, benzalkonium chloride, benzyl alcohol, alkyl paraben, catechol, or cyclohexanol; (iv) amino acids, such as e.g. histidine, arginine; (v) peptides, preferably up to 10 residues such as polylysine; (vi) proteins, such as bovine or human serum albumin; (vii) hydrophilic polymers such as polyvinylpyrrolidone; (viii) monosaccharides, disaccharides, polysaccharides and/or other carbohydrates including glucose, mannose, sucrose, mannitol, trehalose, sorbitol, aminodextran or polyamidoamines; (ix) chelating agents, e.g. EDTA; (x) salt-forming ions such as sodium; (xi) metal complexes (e.g. Zn-protein complexes); and/or (xii) ionic and non-ionic surfactants such as TWEEN™, PLURONICS™ or polyethylene glycol (PEG).

Many of the exemplary compounds have different functions and may, e.g., act as carrier and as diluent. It is also to be understood that the composition may include more than one of each carrier, diluent or excipient.

The binding member, the nucleic acid sequences or the vector may be provided on solid support materials such as beads and microparticles. Typically, a binding member molecule is linked to such carrier via a covalent bond (optionally involving a linker), a non-covalent bond or both. The beads and microparticles can include, for example, starch, cellulose, polyacrylate, polylacetate polyglycolate, poly(lactide-co-glycolide), latex, or dextran.

In one embodiment, a pharmaceutical composition is provided, which includes the binding member, the nucleic acid sequences or the vector as described above. The composition may furthermore include one or more additional therapeutically active compounds in a therapeutically effective amount. The additional therapeutically active compound is in some embodiments a compound active against a TNF-mediated disease.

Therapeutic Applications

A molecule as described herein, in particular the binding member (such as an antibody), the nucleic acid molecule or the vector, is useful as a medicament. Typically, such a medicament includes a therapeutically effective amount of a molecule as provided herein. Accordingly, a respective molecule can be used for the production of a medicament useful in the treatment of one or more TNF alpha-related disorders.

In one aspect, a method of treating an TNF alpha-related disorder is provided. The method includes the steps of administering a pharmaceutically effective amount of a molecule as described herein, in particular the antibody, to a subject in need thereof. In one embodiment, the pharmaceutical composition described above, which includes such pharmaceutically effective amount of the binding member, e.g. antibody, is administered to the subject. The medicament referred to above may be administered to a subject.

The subject in need of a treatment can be a human or a non-human animal. Typically the subject is a mammal, e.g., a mouse, a rat, rabbit, a hamster, a dog, a cat, a monkey, an ape, a goat, a sheep, a horse, a chicken, a guinea pig or a pig. In typical embodiments, the subject is diagnosed with a TNF alpha-related disorder or may acquire such a disorder. In case of an animal model, the animal might be genetically engineered to develop a TNF alpha-related disorder. In an animal model an animal may also be genetically engineered in such a way that it shows the characteristics of a TNF alpha-mediated disease.

A variety of TNF alpha-related disorders are known, in which an antagonist of TNF alpha has shown a therapeutic effect. In some embodiments the TNF alpha-related disorder is proliferative diabetic retinopathy (LIMB GA et al. Distribution of TNF alpha and its reactive vascular adhesion molecules in fibrovascular membranes of proliferative diabetic retinopathy. Br J Ophthalmol. 1996 February; 80(2): 168-73). In some embodiments the TNF alpha-related disorder is at least one of gouty arthritis, acute gouty arthritis and chronic gouty arthritis (TAUSCHE A K et al, Severe gouty arthritis refractory to anti-inflammatory drugs: treatment with anti-tumour necrosis factor alpha as a new therapeutic option. Ann Rheum Dis. 2004 October; 63(10): 1351-2). The TNF alpha-related disorder is in some embodiments Schnitzler syndrome. In some embodiments the TNF alpha-related disorder is systemic juvenile idiopathic arthritis (KOTANIEMI K et al, Long-term efficacy of adalimumab in the treatment of uveitis associated with juvenile idiopathic arthritis. Clin Ophthalmol. 2011;5:1425-9, Epub 2011 Oct. 3). In some embodiments the TNF alpha-related disorder is rheumatoid arthritis (PARAMESWARAN, N. and PAIAL S. Tumor Necrosis Factor-a Signaling in Macrophages. Crit Rev Eukaryot Gene Expr. 2010; vol. 20(2), pp. 87-103). The TNF alpha-related disorder may also be urticaria (SAND F L and THOMSEN S F. TNF-Alpha Inhibitors for Chronic Urticaria: Experience in 20 Patients. J Allergy (Cairo). 2013; 2013:130905. Epub 2013 Sep. 18). In some embodiments the TNF alpha-related disorder is vasculitis (CHUNG S A and SEO P. Advances in the use of biologic agents for the treatment of systemic vasculitis. Curr Opin Rheumatol. 2009 January; 21(1):3-9). In some embodiments the TNF alpha-related disorder is type 1 diabetes or type 2 diabetes. The TNF alpha-related disorder is in some embodiments recurrent multifocal osteomyelitis. In some embodiments the TNF alpha-related disorder is relapsing polychondritis (CARTER J D. Treatment of relapsing polychondritis with a TNF antagonist. J Rheumatol. 2005 July; 32(7):1413). The TNF alpha-related disorder is in some embodiments cyropyrin-associated periodic syndrome (CAPS). In some embodiments the TNF alpha-related disorder is Behçet's disease (PERRA D et al. Adalimumab for the treatment of Behçet's disease: experience in 19 patients. Rheumatology (Oxford). 2012 October; 51(10): 1825-31. Epub 2012 Jun. 20). In some embodiments the TNF alpha-related disorder is familial mediterranean fever. The TNF alpha-related disorder may also be chronic obstructive pulmonary disease (COPD). In some embodiments the TNF alpha-related disorder is polymyalgia rheumatica. In some embodiments the TNF alpha-related disorder is based on one or more mutations of NACHT, LRR and PYD domains-containing protein 3 (NALP3). In some embodiments the TNF alpha-related disorder is pyoderma gangrenosum (PATEL F et al. Effective Strategies for the Management of Pyoderma Gangrenosum: A Comprehensive Review. Acta Derm Venereol. 2014 Nov. 12). The TNF alpha-related disorder is in some embodiments chronic idiopathic urticaria. In some embodiments the TNF alpha-related disorder is psoriasis (see, e.g., CORDORO, KM and FLEDMAN S R. TNF-alpha inhibitors in dermatology. Skin Therapy Letter 2007, vol. 12, pp. 4-6). In some embodiments the TNF alpha-related disorder is osteoarthritis. In some embodiments the TNF alpha-related disorder is wet age-related macular degeneration. In some embodiments the TNF alpha-related disorder is dry eye syndrome. The TNF alpha-related disorder is in some embodiments synovitis-acne-pustulosis-hyperostosis-osteitis syndrome. In some embodiments the TNF alpha-related disorder is macrophage activation syndrome. In some embodiments the TNF alpha-related disorder is periodic fever (Di Gangi M et al. Long-term efficacy of adalimumab in hyperimmunoglobulin D and periodic fever syndrome. Isr Med Assoc J. 2014 October; 16(10):605-7). The TNF alpha-related disorder is in some embodiments adenitis. In some embodiments the TNF alpha-related disorder is pharyngitis, or aphthous ulcer syndrome. The TNF alpha-related disorder is in some embodiments adult-onset Still's disease. The TNF alpha-related disorder may also be mevalonate kinase deficiency. In some embodiments the TNF alpha-related disorder is uveitis (KOTANIEMI K et al, Long-term efficacy of adalimumab in the treatment of uveitis associated with juvenile idiopathic arthritis. Clin Ophthalmol. 2011;5:1425-9. Epub 2011 Oct. 3). In some embodiments the TNF alpha-related disorder is inflammatory bowel disease (PARAMESWARAN, N. and PAIAL S. Tumor Necrosis Factor-a Signaling in Macrophages. Crit Rev Eukaryot Gene Expr. 2010; vol. 20(2), pp. 87-103). The TNF alpha-related disorder is in some embodiments atherosclerosis (PARAMESWARAN, N. and PAIAL S. Tumor Necrosis Factor-a Signaling in Macrophages. Crit Rev Eukaryot Gene Expr. 2010; vol. 20(2), pp. 87-103). In some embodiments the TNF alpha-related disorder is TNF-receptor associated periodic syndrome (TRAPS). In some embodiments the TNF alpha-related disorder is ankylosing spondylitis (PARAMESWARAN, N. and PAIAL S. Tumor Necrosis Factor-a Signaling in Macrophages. Crit Rev Eukaryot Gene Expr. 2010; vol. 20(2), pp. 87-103). The TNF alpha-related disorder may also be hidradenitis suppurativa (Brunasso A M, Massone C. Treatment of hidradenitis suppurativa with tumour necrosis factor-alpha inhibitors: An update on infliximab. Acta Derm Venereol. 2011, vol. 91(1), pp.70; Sotiriou E. et al, Etanercept for the treatment of hidradenitis suppurativa, Acta Derm Venereol. 2009, vol. 89(1), pp. 82-83). In some embodiments the TNF alpha-related disorder is psoriasis (PARAMESWARAN, N. and PAIAL S. Tumor Necrosis Factor-a Signaling in Macrophages. Crit Rev Eukaryot Gene Expr. 2010; vol. 20(2), pp. 87-103). In some embodiments the TNF alpha-related disorder is acne vulgaris.

The term "CAPS" or cryopyrin-associated periodic syndrome is to be understood to include each of familial cold autoinflammatory syndrome (FCAS), Muckle-Wells syndrome (MWS) and neonatal-onset multisystem inflammatory disease, also known as chronic infantile neurological, cutaneous and articular (CINCA) syndrome.

The pharmaceutical composition may be applied by one or more of various suitable routes of administration. Administration can for instance be conducted parenterally. In some embodiments administration is carried out intramuscularly. In some embodiments administration is carried out intravenously as a bolus or by continuous infusion. Administration is in some embodiments conducted intraarticularly. In some embodiments administration is done intrasynovially. Administration may in some embodiments be subcutaneously. In some embodiments administration is carried out topically, e.g., to the skin or the eye. Administration is in some embodiments carried out rectally. In some embodiments administration is done dermally such as intradermally, subcutaneously or transdermally. Administration can in some embodiments be performed locally. Further suitable modes of administration include, but are not limited to intracerebrally, intracerebrospinally, intrathecally, epidurally, or intraperitoneally; orally; urogenitally; intravitreally; systemically; intravenously; intraocularly; oticly; intranasally; by inhalation; sublingually; buccally, for example. Preferred are the topical, rectal, local, intranasal, intravenous and/or intradermal routes of administration.

A binding member disclosed herein, a nucleic acid sequence, a vector or a host cell disclosed herein can be combined with one or more further therapeutically effective compounds. Such a compound may in some embodiments be capable of disrupting signalling via a TNF-alpha receptor. A respective compound may in some embodiments be capable of inhibiting one or more additional targets such as, e.g., other mediators of inflammatory responses. Such compound(s) can be administered simultaneously or sequentially.

For therapeutic applications, the binding member may also be radiolabelled or linked to a toxin or linked to another effector function as described above.

It is to be understood that the outlined above also applies to T-bodies.

Diagnostic Applications and/or Detection Purposes

A binding member as disclosed herein may be used for detection or diagnostic purposes in vivo and/or in vitro. For example, a wide range of immunoassays involving antibodies for detecting the expression in specific cells or tissues are known to the skilled person. Likewise, any binding member, the nucleic acid sequence, the vector and/or the host cell described in the preceding text can be used accordingly as detailed in this section.

For such applications the binding member, e.g. the antibody, the nucleic acid sequence, the vector or the host cell disclosed herein may include a detectable label. In some embodiments the binding member, the nucleic acid sequence, the vector or the host cell disclosed herein does not include a detectable label. As an illustrative example, an unlabelled antibody may be used and detected by a secondary antibody specifically binding to an epitope on the binding member, e.g. antibody, described herein.

In some embodiments the binding member, nucleic acid sequence, vector and/or host cell is coupled to one or more substances that can be recognized by a detector substance. As an example, the binding member may be covalently linked to biotin, which can be detected by means of its capability to bind to streptavidin. Likewise, the nucleic acids and/or vectors disclosed herein can be used for detection or diagnostic purposes, e.g., by using labelled fragments thereof as probes in hybridization assays.

In certain embodiments, any of the molecules provided herein, in particular the antibody, is useful for detecting the presence of TNF alpha in a sample, preferably a sample of biological origin. The term "TNF alpha" as used in this context includes full-length TNF alpha, fragments thereof and/or precursors thereof, i.e. transmembrane TNF alpha and soluble TNF alpha. The term "detecting" encompasses quantitative and/or qualitative detection. In certain embodiments a biological sample includes a cell or tissue from human patients. Non limiting examples of biological samples include blood, urine, cerebrospinal fluid, biopsy, lymph and/or non-blood tissues.

In certain embodiments, the method includes contacting the biological sample with a binding member to TNF alpha (such as an anti-TNF alpha antibody) as described herein under conditions permissive for binding of the inhibitor to its target TNF alpha, if present, and detecting the inhibitor-target complex. Such method may be an in vitro or in vivo method. In one embodiment such binding member is used to select subjects eligible for therapy with the binding members described herein, e.g., where TNF alpha is a biomarker for selection of patients. Similarly, instead of the binding member, such method may involve the use of a T-body described herein.

In another aspect, the binding member, e.g. an antibody, is used in cosmetic applications, e.g., for improving the aesthetic appearance of skin.

Likewise, a T-body, a nucleic acid sequence, a vector and/or a host cell described above can be used accordingly as detailed above.

Article of Manufacture

In a further aspect, an article of manufacture (i.e., a kit) is provided. The article of manufacture includes matter, e.g. material, useful for (i) the treatment, prevention of delay of progression of TNF alpha related disorders; (ii) diagnostic of (iii) cosmetic purposes. The article of manufacture may include instructions for use and one or more containers. Suitable containers include, for example, bottles, vials, syringes, cartridges, plates and test tubes and may be made from a variety of materials such as glass or plastic. At least one container holds a composition that includes a binding member as disclosed herein. The container may have a sterile access port. A respective container is typically labelled.

The reagents are typically provided in predetermined amounts of dry powders, usually lyophilized, including excipients which after dissolution will provide a reagent solution having the appropriate concentration. Other additives such as stabilizers and/or buffers may also be included. If the binding member is labelled with an enzyme, the kit will typically include the according substrates and cofactors.

The instructions for use may provide indications that the composition is used for the treatment, prevention and/or delay of progression of a disorder of choice; or instructions for performing a detection or diagnostic assay. The instructions may be provided on a label and/or on a package insert.

SEQUENCES REFERRED TO

The sequences disclosed herein are:

```
VL of scFv1
                                          SEQ ID No: 1
EIVMTQSPSTLSASVGDRVIITCQASQSISSYLAWYQQKPGKAPKLLIYW
ASTLASGVPSRFSGSGSGTEFTLTISSLQPDDFATYYCQSYYYTSNNSDG
FWAFGQGTKLTVLG

VH of scFv1
                                          SEQ ID No: 2
EVQLVESGGGLVQPGGSLRLSCKASGIDFSNSGITWVRQAPGKGLEWVGY
IYPGFGIRNYANSVRGRFTISRDTSKNTVYLQMNSLRAEDTAVYYCARDP
IYASSSGYADIWGQGTLVTVSS

CDR-L1 of scFv1
                                          SEQ ID No: 3
QASQSISSYLA

CDR-L2 of scFv1
                                          SEQ ID No: 4
WASTLAS

CDR-L3 of scFv1
                                          SEQ ID No: 5
QSYYYTSNNSDGFWA

CDR-H1 of scFv1
                                          SEQ ID No: 6
IDFSNSGIT

CDR-H2 of scFv1
                                          SEQ ID No: 7
YIYPGFGIRNYANSVRG

CDR-H3 of scFv1
                                          SEQ ID No: 8
DPIYASSSGYADI scFv1
                                          SEQ ID No: 9
EIVMTQSPSTLSASVGDRVIITCQASQSISSYLAWYQQKPGKAPKLLIYW
ASTLASGVPSRFSGSGSGTEFTLTISSLQPDDFATYYCQSYYYTSNNSDG
```

-continued
```
FWAFGQGTKLTVLGGGGGSGGGGSGGGGSGGGGSEVQLVESGGGLVQPGG
SLRLSCKASGIDFSNSGITWVRQAPGKGLEWVGYIYPGFGIRNYANSVRG
RFTISRDTSKNTVYLQMNSLRAEDTAVYYCARDPIYASSSGYADIWGQGT
LVTVSS linker
                                          SEQ ID No: 10
GGGGSGGGGSGGGGSGGGGS DLX105
                                          SEQ ID No: 11
MADIVMTQSPSSLSASVGDRVTLTCTASQSVSNDVVWYQQRPGKAPKLLI
YSAFNRYTGVPSRFSGRGYGTDFTLTISSLQPEDVAVYYCQQDYNSPRTF
GQGTKLEVKRGGGGSGGGGSGGGGSSGGGSQVQLVQSGAEVKKPGASVKV
SCTASGYTFTHYGMNWVRQAPGKGLEWMGWINTYTGEPTYADKFKDRFTF
SLETSASTVYMELTSLTSDDTAVYYCARERGDAMDYWGQGTLVTVSS
```

The following are examples, illustrating the methods and compositions disclosed herein. It is understood that various other embodiments may be practiced, given the general description provided above.

EXAMPLES

Example 1

Identification of TNF Alpha Neutralizing scFvs

Immunization of rabbits: Rabbits were immunized with recombinant human (rh) TNF alpha (Peprotech, USA, cat. no. 300-01A). Lymph nodes were extracted after the final boost and the cells were cryopreserved.

Flow cytometry sorting of rabbit B cells and culturing: TNF alpha-specific memory B cells were sorted as single cells into 96-well microplates using FACSAria III (BD Biosciences). Single B cell clones were cultured in the presence of feeder cells and conditioned medium containing 10% fetal calf serum (FCS).

In total, 3150 single B cell clones were sorted, cultured and cell culture supernatants were analyzed by ELISA for the presence of anti-TNF alpha-specific IgGs. Briefly, rhTNF alpha (Peprotech, cat. no. 300-01A) was coated at a concentration of 2 mcg/mL overnight at 4° C. on Maxisorp 96-well microplates in PBS. After blocking with 5% non-fat dry milk, cell culture supernatants were added. TNF alpha-specific IgGs were detected by anti-rabbit IgG-HRP (Southern Biotech, cat. no. 4050-05). The ELISA was developed with BM Blue POD substrate (Roche Applied Science). In total, 566 selected TNF alpha-specific IgG-producing B cell clones were identified and IgG antibodies were further analyzed for their neutralizing capacity in the PK-15 cell assay. Two hundred IgG-producing B cell clones were found to neutralize the cytotoxic activity of rhTNF alpha.

Sequencing of TNF alpha-neutralizing IgGs: all rabbit B cell clones producing neutralizing anti-TNF alpha IgG antibodies were subjected to mRNA isolation using the RNeasy Mini Kit (Qiagen Germany, cat. no. 74106). The mRNA was used as a template for reverse transcription according to the manufacture's protocol (OneStep RT-PCR kit, Qiagen Germany, cat. no. 210212). Subsequently, PCR reactions using oligonucleotides to specifically amplify rabbit IgG heavy and light chain encoding sequences were carried out (Biometry Thermocycler T3). Heavy and light chain PCR fragments were independently sequenced (ABI, Sanger 3730×1;

Microsynth AG, Balgach, Switzerland), and obtained nucleotide sequences were translated into amino acid sequences using EMBOSS Transeq and aligned using CLUSTALW2.

Construction of anti-TNF alpha scFv genes and scFv protein expression: rabbit IgG CDR regions of the variable light and the variable heavy chains as defined above were identified and grafted onto the human light and heavy chain acceptor frameworks. In some, point mutations were introduced. Bacterial expression vectors were generated encoding scFv proteins with the N-terminal variable light chain linked by the sequence SEQ ID No: 10 to the C-terminal variable heavy chain. ScFv proteins were expressed in *E.coli* BL21 (DE3); Novagen, USA, cat. no. 69450-3) as inclusion bodies, which were purified, solubilized and the proteins were refolded. The refolded scFvs were purified by size exclusion chromatography and monomeric peak fractions corresponding to approximately 26 kDa were collected. Purified scFvs were analyzed for TNF alpha binding by ELISA. ScFvs were further evaluated to determine the TNF alpha neutralizing capacity in a PK-15 cell assay. By this procedure, out of 72 tested scFvs, five TNF alpha-specific scFvs were identified as potent inhibitors of human TNF alpha.

Example 2

Binding of Human Soluble and Transmembrane TNFalpha

Figure 1B:
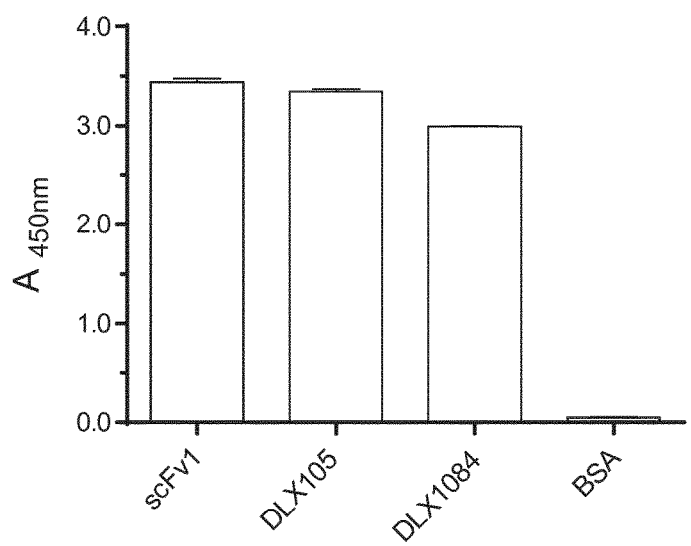
FIG. 1B shows that all scFvs immobilized to the ELISA plate were properly refolded and recognizable by protein L-HRP.

Firstly, the specific recognition of TNF alpha was confirmed by ELISA (FIG. 1). Briefly, rhTNF alpha was coated at a concentration of 2 mcg/mL, overnight at 4° C. on Maxisorp 96-well microplates in PBS. After blocking with 5% non-fat dry milk, increasing concentrations of all five preselected scFvs (10 to 3000 ng/mL) were added, and scFvs were detected by Protein L-HRP (Sigma-Aldrich, cat. no. P3226). The ELISA was developed with BM Blue POD substrate (Roche Applied Science). The TNF alpha-specific scFv DLX105 was used as positive control. DLX1084, a scFv of irrelevant specificity was used as a negative control. The FIG. 1A shows that scFv1 specifically binds to rhTNF alpha. All scFvs, when directly immobilized on the microplates, were recognized by Protein L-HRP (FIG. 1B). This shows that (i) the scFvs were properly refolded, (ii) the control scFv DLX1084 did riot bind rhTNF alpha, and (iii) confirms that the identified scFv1 is specific for rhTNF alpha.

Recognition of the naturally produced human TNF alpha was assessed by a sandwich ELISA. The natural form of human TNF alpha was derived from the human THP-1 monocyte cell line (DSMZ Germany, cat no ACC 16). THP-1 cells were cultured in 6-well tissue culture plates and stimulated with 10 ng/ml of phorbol 12-myristate 13-acetate (PMA; Sigma-Aldrich, cat no P1585) for 6 hours, and subsequently stimulated with 1 mcg/mL of LPS (Sigma-Aldrich, cat no L4391) for 16 hours at 37° C. Cell supernatants were harvested and secreted TNF alpha was quantified using the human TNF alpha/TNFSF1A ELISA DuoSet (R&D Systems, cat no DY210). The scFv samples were immobilized on 96-well microplates (Maxisorp, Nunc) at 5 mcg/mL in PBS pH 7.2. After blocking and washing, the natural form of human TNF alpha or recombinantly expressed human TNF alpha (Peprotech, cat. no. 300-01A) were applied at final concentrations of 5 ng/mL. The bound TNF alpha was detected with the biotinylated polyclonal anti-TNF alpha antibody and streptavidin-HRP (BD Pharmingen, cat no 554060). All five selected scFvs bind equally well both rhTNF alpha and the natural form of human TNF alpha.

Figure 4A:
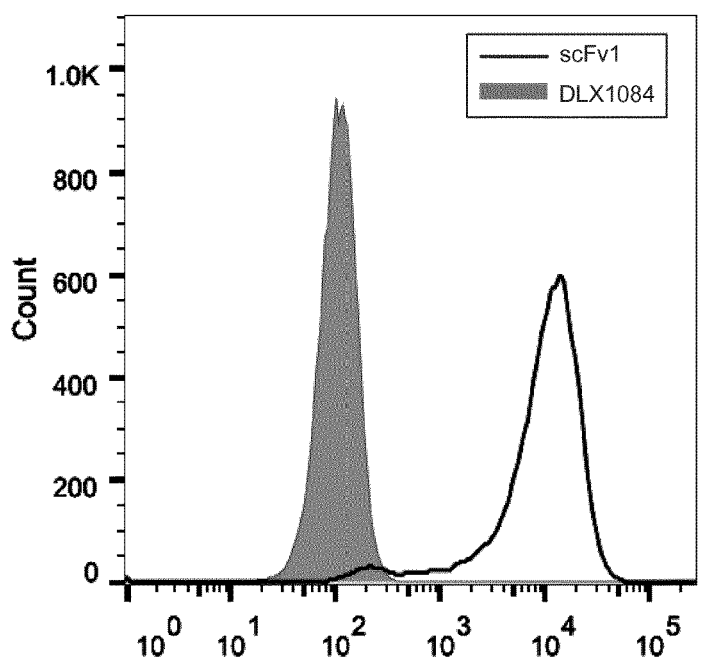
FIG. 4A depicts the flow cytometry analysis of scFv1 (plain line) and the negative control scFv DLX1084 (filled histogram) with tmTNF alpha-expressing CHO cells.

Recognition of transmembrane TNF alpha: CHO cells expressing the Δ1-12 variant of human TNF alpha, which remains membrane associated, were stained with the five selected scFv or control scFvs and analyzed by flow cytometry. The cells were incubated with increasing amounts of scFv, and bound scFvs detected using biotinylated protein L and subsequent staining with PE-labelled streptavidin. All five scFv samples including scFv1 efficiently bind tmTNF alpha, while the negative control scFv DLX1084 did not bind tmTNF alpha. The flow cytometry histograms for the scFv1 and the negative control scFv DLX1084 are shown in FIG. 4A.

Example 3

Neutralization of Soluble and Trans-membrane Human TNF Alpha

Figure 2:
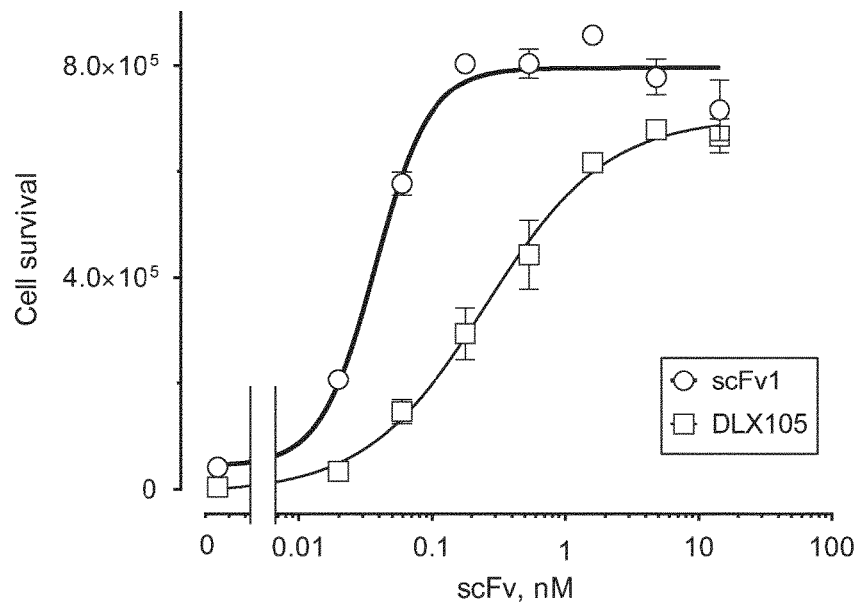
FIG. 2 is a graph showing the inhibition of rhTNF alpha-mediated PK-15 cell cytotoxicity by scFvs at low picomolar concentrations. Serial dilutions of scFv1 (open circle, ○), or the positive control scFv DLX105 (open square, □) were pre-incubated with soluble TNF alpha, followed by incubation with PK-15 cells.
Figure 3:
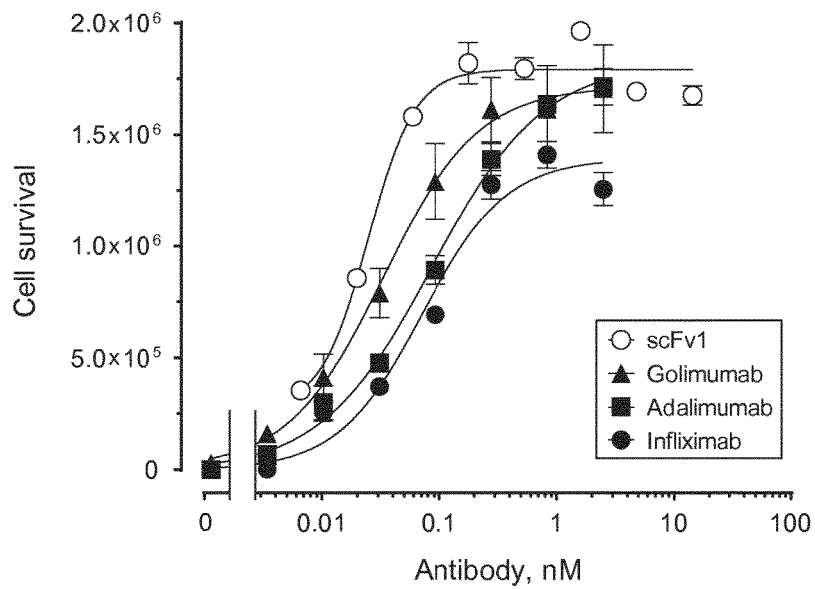
FIG. 3 is a graph showing the superior inhibition of soluble TNF alpha-mediated PK-15 cell cytotoxicity by the scFv1 antibody fragment compared to other, commercially available, TNF alpha antagonists of the IgG type. Serial dilutions of scFv1 (open circle, ○), golimumab (filled triangle, ▲), adalimumab (filled square, ■) or infliximab (filled circle, ●) were pre-incubated with soluble TNF alpha, followed by incubation with PK-15 cells.

Full-length antibodies and scFvs were tested for their TNF alpha neutralization capacity in a PK-15 cell assay (porcine kidney epithelial cells, DSMZ, Germany, cat. no. ACC640). The positive control scFv DLX105 as well as commercially available antibodies (infliximab, golimumab and adalimumab) were used for comparison. The CellTiter-Glo® Luminescent Cell Viability Assay was adapted to determine the $IC_{50}$ values for TNF alpha-specific scFvs. In this assay, generation of a luminescent signal is proportional to the amount of ATP present which is directly proportional to the number of living cells present in culture. Briefly, the soluble form of rhTNF alpha (1.4 pM) was pre-incubated with increasing concentrations of scFvs (200 pg/mL to 3 mcg/mL), and added to the PK-15 cells (10.000/well). The CellTiter-Glo® reagent (Promega, cat. no. G7572) was used according to manufacturer's instructions. Luminescence was measured on a GloMax® 96 Microplate Luminometer Inhibition curves were plotted and the $IC_{50}$ values were calculated using GraphPad Prism® software, version 6.04. scFv1 efficiently blocked the cytotoxicity of rhTNF alpha with an $IC_{50}$ of 30±6 pM, whereas the $IC_{50}$ value for the monovalent positive control scFv DLX105 (260±34 pM) was significantly higher (FIG. 2, Table 1). ScFvs 2-5 potently inhibited the cytotoxic activity of rhTNF alpha with $IC_{50}$ values ranging from 25 pM to 40 pM. The $IC_{50}$ values for all five monovalent scFvs were comparable to those of marketed bivalent antibodies infliximab, adalimumab and golimumab (FIG. 3).

In Example 2, it is shown that all selected scFvs bind the transmembrane form of TNF alpha. In order to investigate whether the scFvs neutralize the biological activity of tmTNF alpha, the cytotoxic effect of tmTNF alpha to HEK-Dual TNF alpha-sensitive cells (InvivoGen, cat. no. hkd-tnfa) was exploited. HEK-Dual TNF alpha-sensitive cells were designed to monitor the bioactivity of TNF alpha by assessing NF-kB activation. The cells were derived from the human embryonic kidney 293 cells by stable co-transfection of two NF-kB-inducible reporter constructs. As a result, HEK-Dual TNF alpha-sensitive cells secrete luciferase and embryonic alkaline phosphatase in response to TNF alpha induced NF-kB activation. Both reporter gene products are measured in the cell culture supernatant using Quanti-Luc (InvivoGen, cat. no. rep-q1c1) and Quanti-Blue (InvivoGen, cat. no. rep-qb1). CHO cells expressing tmTNF alpha were plated at 10,000 cells/well in 96 well flat bottom microplates in 100 μl RPMI 1640 containing 5% of FCS.

Figure 4B:
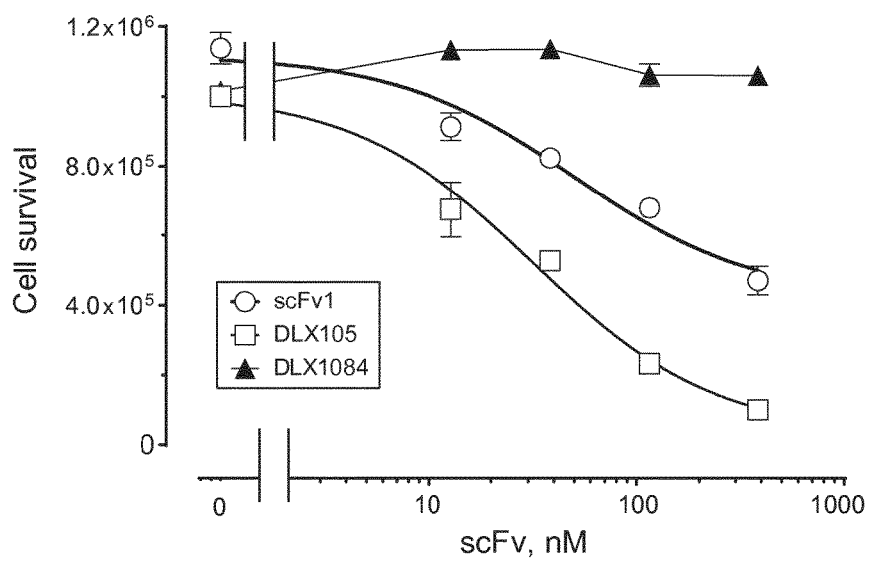
FIG. 4B depicts cell survival at serial dilutions of scFv1 (open triangle), the positive control scFv DLX105 (open square), and the negative control scFv DLX1084 (filled triangle), which were incubated with CHO cells expressing tmTNF alpha, followed by addition of HEK-Dual TNF alpha-sensitive cells.

Serial dilutions of scFv1, the positive control scFv DLX105 or the negative control scFv DLX1084 (10 to 300 nM) were incubated with tmTNF alpha-expressing CHO cells at 37° C. for 20 min. The HEK-dual cells were then added at 20,000 cells/well, and co-cultured at 37° C. for 24 h. Resulting cell culture supernatants were used to measure the activities of luciferase and secreted embryonic alkaline phosphatase Inhibition curves were plotted and the $IC_{50}$ values were calculated using GraphPad Prism® software, version 6.04. The five selected scFvs inhibited trans-membrane TNF alpha activity with $IC_{50}$ values ranging from 10 nM to 50 nM, with scFv5 having the highest $IC_{50}$ value. scFv1 and the positive control scFv DLX105 inhibited the activity of tmTNF alpha with an $IC_{50}$ of 50 nM and 32 nM, respectively (FIG. 4B, table 1). Similar results were obtained when Quanti-Blue was used to measure the alkaline phosphatase activity. Thus, under these experimental conditions 400 nM of scFv1 inhibited 50% of the tmTNF alpha activity.

TABLE 1

Neutralization potencies against soluble and transmembrane TNF alpha

| scFv | Soluble TNF alpha | Transmembrane TNF alpha |
|---|---|---|
| scFv1 | 30 ± 6 pM | 50 nM* |
| positive control scFv DLX105 | 260 ± 34 pM | 32 nM* |

*similar results were obtained in 2 independent experiments.

Example 4

Species and TNF Alpha Family Cross-reactivity of scFvs

The cross-reactivity profile of the five selected scFvs to TNF alpha homologs of other species than human beings was assessed using ELISA. The following recombinantly expressed TNF alpha proteins were investigated: rhesus macaque (R&D Systems, USA, cat. no. 1070-RM-025/CF), cynomolgus monkey (Sinobiological, cat.no. 90018 CNAE), canine (Kingfisher Biotech, USA, cat. no. RP0261D-025) and feline (R&D systems, cat. No, 2586FTCF), rabbit (Kingfisher, cat. no RPO429U), rat (Peprotech, cat. no 400-14) murine (Peprotech, cat. no 315-01A), guinea pig (R&D Systems, cat. no 5035-TG-025/CF), porcine (R&D Systems, cat. no 690-PT-025/CF). Briefly, proteins were coated at a concentration of 2 mcg/mL over night at 4° C. on Maxisorp 96-well microplates in PBS pH 7.2. After blocking with 5% non-fat dry milk, increasing concentrations of scFv (0.1, 0.3 and 1.0 mcg/mL) were added to the wells. Successful coating of every protein was separately confirmed with TNF alpha-specific control antibodies. Whereas scFv1 was detected by Protein L-HRP (Sigma-Aldrich, USA, cat. no. P3226), the full-length IgG control antibodies were detected by either Streptavidin-HRP (BD Pharmingen, USA, cat. no. 554060) or other eligible secondary antibodies labelled with HRP. The ELISA was developed with BM Blue POD substrate (Roche Applied Science) and the absorbance was measured at 450 nm. The cross-reactivity of scFvs 1-5 was compared to the scFv DLX2481. DLX2481 is a variant of the EP-34 scFv as described in WO2009/155723 (ESBATech, an Alcon Biomedical Research Unit LLC), including several point mutations in the framework regions. scFv1, scFv3 and scFv4 specifically recognized five species orthologs of TNF alpha, namely human, rhesus macaque, cynomolgus monkey, feline and canine TNF alpha proteins. scFv2 specifically recognized rhTNF alpha, but did not cross-react with any other tested species. The scFv DLX2481 recognized only recombinant human TNF alpha. In addition, the cross-reactivity of scFv1 to TNF family members was measured by a direct ELISA with coated recombinant human lymphotoxin α2/β1 (R&D systems, USA, cat. No 679-TX-010/CF), recombinant human lymphotoxin α1/β2 (R&D systems, cat. No 678-LY-010/CF), recombinant human CD40 ligand/TNFSF5 (R&D systems, cat. No. 6420-CL-025/CF) and recombinant human TNF beta/TNFSF1 (R&D systems, cat. No. 211-TB-010/CF). scFv1 did not cross-react with these TNF family proteins up to a concentration of 40 nM.

Example 5

Stability of scFvs

Two different processes can be observed that may affect the stability of scFvs. Firstly, the scFv could be prone to dimerization, often followed by oligomerization and further aggregation and precipitation. Secondly, scFv degradation, leading to smaller fragments, can occur over time.

The stability of the five selected scFvs formulated in PBS pH 7.2 upon storage at different temperature conditions was investigated. The scFv were stored at 10 mg/mL concentration at 4° C., 22° C., 37° C. and −20° C. in 1.5 mL polypropylene tubes. At indicated time points, each sample was inspected visually and protein concentration was measured at 280 nm. Whereas scFv 3 and 4 showed lower stability at 4° C. and at 37° C. after 1 week of incubation, no visible protein precipitation and no significant protein loss was observed for scFv1. The samples were analyzed by SE-HPLC to determine the levels (%) of monomers, dimers and high molecular weight oligomers in relation to the total peak area: a TOSOH TSKgel G2000 SWXL column, phase diol, L×I.D. 30 cm×7.8 mm, 5 μm particle size (Sigma, cat no 08540) was used. 5 μL of scFv1 at 1 mg/mL were loaded. As mobile phase PBS pH 7.2 was chosen.

The SE-HPLC analysis showed no detectable low molecular weight degradation products in above described experimental conditions. No significant dimerization of scFv1 was observed upon storage for 4 weeks at 4° C., 22° C. and −20° C. scFv1 formed up to 2.61%, 6.09%, 8.75% and 11.02% of dimers after 1, 2, 3 or 4 weeks of storage at 37° C., respectively (Table 2), and only minor amounts of high molecule weight molecules were observed upon storage for 3 and 4 weeks at 37° C.

TABLE 2 scFv1 monomer content (%) measured using SE-HPLC upon storage at indicated conditions

| | Day 7 | Day 14 | Day 21 | Day 28 |
|---|---|---|---|---|
| scFv1, 10 mg/mL, 4° C. | 99.73 | 99.64 | 99.57 | 99.15 |
| scFv1, 10 mg/mL, 22° C. | 99.52 | 99.17 | 98.89 | 98.57 |
| scFv1, 10 mg/mL, 37° C. | 96.54 | 92.01 | 88.22 | 84.68 |
| scFv1, 10 mg/mL, −20° C. | nd* | nd | nd | 99.09 |

*nd, not determined.

The stability measurement was extended for scFv1 to up to 6 months. After six months at 4° C., the scFv1 preparation contained 91.17% of monomers.

The thermal stability of scFv1 was also assessed by differential scanning fluorimetry (DSF). scFv1 at 0.54 mg/mL formulated in PBS pH 7.2 was heated from 30° C. to 95° C. at a scan rate of 1° C/5 seconds in a real time PCR device (Corbett, Rotor-Gene) in the presence of 20× SYPRO® Orange (Sigma-Aldrich, cat. no. S5692, 5000×) in PBS pH7.2. The fluorescence values were measured (excitation wavelength of 470 nm; emission wavelength of 555 nm) during the gradient run. The midpoint melting temperatures (Tm) of scFv1 calculated using Rotor-Gene 6000 Series Software 1.7. was 76.0° C. for scFv1.

Proteinaceous biologics may become exposed to freeze/thaw stress during manufacturing, storing and shipping which may cause aggregation and degradation. In order to assess stability of scFv1 during freeze/thaw cycles, it was formulated in PBS pH 7.2 at 10 mg/mL in 1.5 mL polypropylene tubes. The vials were submerged into liquid nitrogen for 5 min. For thawing they were incubated in a water bath at room temperature for 10 min. One, 3, 5, 7 or 10 freeze/thaw cycles were performed and samples were analyzed by SE-HPLC as mentioned above. Virtually 100% of scFv1 remained monomeric after 10 freeze/thaw cycles and no protein loss or precipitation was observed.

For further characterization, scFv1 was selected from the pool of five preselected scFvs due to its outstanding stability parameters, its high potency and its broad cross-reactivity spectrum.

Example 6

Stability in 90% Human Serum

The five scFv scFv1-5 were diluted to 0.1 mg/mL in PBS, pH 7.2. An aliquot of scFv was added to human serum (Sigma, cat. no. H4522) to give a final concentration of 10 mcg/mL in 90% v/v human serum. In parallel, scFvs were diluted in PBS, pH 7.2 containing 1% of BSA. The samples were incubated at 4° C. and 37° C. for 1, 4 and 20 hours. The TNF alpha binding capacity of the samples was measured by a direct ELISA with immobilized TNF alpha as described in example 2. Serum-exposed scFv1 was tested at increasing concentrations (20 to 500 ng/mL) and detected by Protein L-HRP. The results indicate that a 20 hours exposure to human serum at 37° C. did not significantly alter the TNF alpha binding capacity of scFv1, and scFv2-5.

Example 7

Solubility of scFvs

The five selected scFvs scFv1-5 were purified and stored in PBS buffer pH 7.2 (Phosphate Buffered Saline 1×, Gibco, Life Technologies™, cat. no. 20012). scFv1 was concentrated using Vivaspin 20 centrifuge concentrators (Sartorius Stedim Biotech, cat. no. VS2001) at room temperature up to 50 mg/mL and analyzed visually and by analytical HPLC (column TOSOH TSKgel G2000 SWXL, cat. no. 08540). The resulting solutions of scFv1 were clear and without any precipitates, and 100% of the protein was monomeric. Thus, the solubility of scFv1 in PBS pH 7.2 is ≥50 mg/mL.

Example 8

Neutralization of Rhesus Macaque, Cynomolgus Monkey and Canine TNF Alpha

ScFv1 was assayed for inhibiting the cytotoxic activity of rhesus macaque, cynomolgus monkey and canine TNF alpha proteins against PK-15 cells as described above. Serial dilutions of scFv1 were preincubated with 50 pg/mL of recombinant rhesus macaque, cynomolgus monkey or canine TNF alpha proteins. The mixtures were added to PK-15 cells, further incubated, and analyzed as described in example 3. ScFv1 was highly potent in neutralizing rhesus macaque, cynomolgus monkey and canine TNF alpha proteins.

Example 9

In vivo Efficacy

The capacity of scFv1 to block the biological activity of human TNF alpha in vivo was demonstrated using Tg1278TNF-ko mouse, a mouse strain which contains a transgene encoding the complete human TNF alpha gene with flanking regions. These mice express normally regulated human TNF alpha in the absence of mouse TNF alpha and exhibit normal development with no apparent pathology.

The susceptibility of mice to Gram-negative bacteria-derived lipopolysaccharide (LPS) is increased by treatment with D-galactosamine (D-gal), a hepatotoxic agent, which increases the sensitivity to the lethal effects of LPS by 100,000 fold. The effect of D-gal is exclusively restricted to hepatocytes where it causes depletion of uracil nucleotides that results in an impaired biosynthesis of RNA and proteins. LPS/D-gal administration in mice leads to consistent mortality observed within 48 hours caused by fulminant liver injury characterized by widespread apoptotic death of hepatocytes which primarily results from TNF alpha signaling through the TNF receptor 1. Treatment of mice with a neutralizing anti-TNF alpha antibody protects them from the lethal effects of LPS/D-gal liver toxicity.

ScFv1 and the positive control scFv DLX105 were administered twice intraperitoneally at doses of 10.0 mg/kg body weight to 8-9 weeks old hTNF alpha transgenic mice 1 h before and 1 h after the i.p. challenge with LPS/D-Gal (10 ng/dose of LPS, 20 mg/dose of D-gal). Two hours after the LPS/D-gal challenge blood samples were taken and serum levels of mouse IL-6 were measured using the Mouse IL-6 DuoSet ELISA kit according to the manufacturer's instructions (R&D Systems, cat no DY406). The negative control group was treated twice intraperitoneally with scFv of irrelevant specificity (negative control scFv) at a 10 mg/kg dose. scFv1 and the positive control scFv DLX105 efficiently protected LPS/D-gal-challenged mice, while the negative control scFv did not (Table 4). Accordingly, mouse serum IL-6 levels were significantly inhibited by scFv1 and positive control scFv DLX105, while the negative control scFv did not inhibit the mouse serum IL-6 (Table 4).

Table 4 shows the protective effect of scFv1, positive control scFv DLX105 and negative control scFv. The survival rates (%) of mice, and serum levels of mouse IL-6 as average values in pg/mL incl. standard deviations are shown.

| Tg1278/ TNFko, n = 6 | Treatment | % survival, 48 h | % survival, 120 h | Survival | serum IL-6 levels, 2 h |
|---|---|---|---|---|---|
| 3♂/3♀ | DLX105 | 83.3 | 66.7 | 4/6 | 603 ± 223 pg/mL |
| 3♂/3♀ | Neg. control scFv | 0 | 0 | 0/6 | 5240 ± 1212 pg/mL |
| 3♂/3♀ | scFv1 | 100 | 83.3 | 5/6 | 787 ± 385 pg/mL |

While there are shown and described presently preferred embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

The invention claimed is:

1. An antibody or fragment thereof having a binding specificity to TNF alpha, the antibody or fragment thereof comprising
   (i) the variable heavy chain CDR-H1, CDR-H2 and CDR-H3 sequences as set forth in SEQ ID Nos: 6, 7 and 8; and
   (ii) the variable light chain CDR-L1, CDR-L2 and CDR-L3 sequences as set forth in SEQ ID Nos: 3, 4 and 5.

2. The antibody or fragment thereof of claim 1, wherein the antibody or fragment thereof has an $IC_{50}$ with regard to human TNF alpha of lower than 50 pM.

3. The antibody or fragment thereof of claim 1, being humanized.

4. The antibody or fragment thereof of claim 1, comprising
   (i) a variable light chain as set forth in SEQ ID No. 1; and/or
   (ii) a variable heavy chain as set forth in SEQ ID No. 2.

5. The antibody or fragment thereof of claim 1, further comprising a linker sequence.

6. The antibody or fragment thereof of claim 5, comprising SEQ ID No. 9.

7. The antibody or fragment thereof of claim 5, wherein the linker sequence is the sequence set forth in SEQ ID No: 10.

8. The antibody or fragment thereof of claim 1, wherein the variable heavy chain further comprises at least one of the following residues:
   (i) Serine (S) at heavy chain amino acid position 12 (according to AHo numbering);
   (ii) Serine (S) or Threonine (T) at heavy chain amino acid position 103 (according to AHo numbering); and/or
   (iii) Serine (S) or Threonine (T) at heavy chain amino acid position 144 (according to AHo numbering).

9. The antibody or fragment thereof of claim 1, being monovalent or multivalent, wherein the antibody or fragment thereof is optionally bispecific.

10. The antibody or fragment thereof of claim 9, wherein the antibody or fragment thereof is a diabody, a single-chain diabody or a tandem scFv.

11. The antibody or fragment thereof of claim 1, remaining at least 93% monomeric after incubation for 1 week at 37° C. at a concentration of 10mg/ml PBS pH7.2.

12. The antibody or fragment thereof of claim 1, being chemically or biologically modified.

13. The antibody or fragment thereof of claim 12, being glycosylated, PEGylated or HESylated.

14. The antibody or fragment thereof of claim 1, wherein the antibody or fragment thereof is a monovalent antibody or fragment thereof.

15. The antibody or fragment thereof of claim 14, wherein the antibody or fragment thereof is a scFv.

16. The antibody or fragment thereof of claim 1, wherein the antibody fragment is a Fab, a Fab', a F(ab)'$_2$, a scFv, or a Fv fragment.

17. A kit comprising the antibody or fragment thereof of claim 1 together with a packaged combination of reagents with instructions.

18. A composition comprising the antibody or fragment thereof claim 1; and further a suitable carrier, diluent or excipient.

19. The composition of claim 18, being a cosmetic, a diagnostic or a pharmaceutical composition.

20. The composition of claim 19, being, a pharmaceutical composition and the carrier being a pharmaceutically acceptable carrier, diluent or excipient.

21. The composition of claim 20, being in a form suitable for parenteral, oral, rectal, systemic, urogenital, topical, intravitreal, intraocular, otic, intranasal, dermal, sublingual, or buccal administration.

22. A method of producing the antibody or fragment thereof of claim 1, the method comprising:
(i) cultivating an isolated host cell comprising a nucleic acid molecule comprising a sequence encoding the antibody or fragment thereof of claim 1 under conditions adequate for recombinant protein expression, thereby allowing the antibody or fragment thereof to be expressed;
(ii) recovering the expressed antibody or fragment thereof; and
(iii) optionally purifying the antibody or fragment thereof.

23. A method of producing the antibody or fragment thereof of claim 1, the method comprising:
(a) contacting a cell-free expression system with a nucleic acid product template, the nucleic acid product template encoding the antibody of fragment thereof according to claim 1;
(b) allowing transcription and translation of the nucleic acid product template to occur, thereby allowing a reaction mixture to be formed;
(c) recovering the antibody or fragment thereof from the reaction mixture; and
(d) optionally purifying the antibody or fragment thereof.

24. A method of detecting the presence of TNF alpha in a biological sample, the method comprising:
(i) contacting the biological sample with the antibody or fragment thereof of claim 1 under conditions permissive for specific binding of the antibody or fragment thereof to TNF alpha, and
(ii) detecting whether a complex between the antibody or fragment thereof and TNF alpha is formed.

* * * * *

```
                        SEQUENCE LISTING

<160> NUMBER OF SEQ ID NOS: 11

<210> SEQ ID NO 1
<211> LENGTH: 114
<212> TYPE: PRT
<213> ORGANISM: Artificial Sequence
<220> FEATURE:
<223> OTHER INFORMATION: VL sequence

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Tyr Tyr Thr Ser Asn
                85                  90                  95

Asn Ser Asp Gly Phe Trp Ala Phe Gly Gln Gly Thr Lys Leu Thr Val
            100                 105                 110

Leu Gly

<210> SEQ ID NO 2
<211> LENGTH: 122
<212> TYPE: PRT
<213> ORGANISM: Artificial Sequence
<220> FEATURE:
<223> OTHER INFORMATION: VH

<400> SEQUENCE: 2

Glu Val Gln Leu Val Glu Ser Gly Gly Leu Val Gln Pro Gly Gly
1               5                   10                  15

Ser Leu Arg Leu Ser Cys Lys Ala Ser Gly Ile Asp Phe Ser Asn Ser
            20                  25                  30

Gly Ile Thr Trp Val Arg Gln Ala Pro Gly Lys Gly Leu Glu Trp Val
        35                  40                  45

Gly Tyr Ile Tyr Pro Gly Phe Gly Ile Arg Asn Tyr Ala Asn Ser Val
    50                  55                  60

Arg Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Ile Tyr Ala Ser Ser Ser Gly Tyr Ala Asp Ile Trp
            100                 105                 110

Gly Gln Gly Thr Leu Val Thr Val Ser Ser
        115                 120

<210> SEQ ID NO 3
```

```
<211> LENGTH: 11
<212> TYPE: PRT
<213> ORGANISM: Oryctolagus cuniculus

<400> SEQUENCE: 3

Gln Ala Ser Gln Ser Ile Ser Ser Tyr Leu Ala
1               5                   10

<210> SEQ ID NO 4
<211> LENGTH: 7
<212> TYPE: PRT
<213> ORGANISM: Oryctolagus cuniculus

<400> SEQUENCE: 4

Trp Ala Ser Thr Leu Ala Ser
1               5

<210> SEQ ID NO 5
<211> LENGTH: 15
<212> TYPE: PRT
<213> ORGANISM: Oryctolagus cuniculus

<400> SEQUENCE: 5

Gln Ser Tyr Tyr Tyr Thr Ser Asn Asn Ser Asp Gly Phe Trp Ala
1               5                   10                  15

<210> SEQ ID NO 6
<211> LENGTH: 9
<212> TYPE: PRT
<213> ORGANISM: Oryctolagus cuniculus

<400> SEQUENCE: 6

Ile Asp Phe Ser Asn Ser Gly Ile Thr
1               5

<210> SEQ ID NO 7
<211> LENGTH: 17
<212> TYPE: PRT
<213> ORGANISM: Oryctolagus cuniculus

<400> SEQUENCE: 7

Tyr Ile Tyr Pro Gly Phe Gly Ile Arg Asn Tyr Ala Asn Ser Val Arg
1               5                   10                  15

Gly

<210> SEQ ID NO 8
<211> LENGTH: 13
<212> TYPE: PRT
<213> ORGANISM: Oryctolagus cuniculus

<400> SEQUENCE: 8

Asp Pro Ile Tyr Ala Ser Ser Ser Gly Tyr Ala Asp Ile
1               5                   10

<210> SEQ ID NO 9
<211> LENGTH: 256
<212> TYPE: PRT
<213> ORGANISM: Artificial Sequence
<220> FEATURE:
<223> OTHER INFORMATION: scFv1

<400> SEQUENCE: 9

Glu Ile Val Met Thr Gln Ser Pro Ser Thr Leu Ser Ala Ser Val Gly
1               5                   10                  15
```

Asp Arg Val Ile Ile Thr Cys Gln Ala Ser Gln Ser Ile Ser Ser Tyr
                20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Tyr Thr Ser Asn
                85                  90                  95

Asn Ser Asp Gly Phe Trp Ala Phe Gly Gln Gly Thr Lys Leu Thr Val
            100                 105                 110

Leu Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
130                 135                 140

Leu Val Gln Pro Gly Gly Ser Leu Arg Leu Ser Cys Lys Ala Ser Gly
145                 150                 155                 160

Ile Asp Phe Ser Asn Ser Gly Ile Thr Trp Val Arg Gln Ala Pro Gly
                165                 170                 175

Lys Gly Leu Glu Trp Val Gly Tyr Ile Tyr Pro Gly Phe Gly Ile Arg
            180                 185                 190

Asn Tyr Ala Asn Ser Val Arg Gly Arg Phe Thr Ile Ser Arg Asp Thr
        195                 200                 205

Ser Lys Asn Thr Val Tyr Leu Gln Met Asn Ser Leu Arg Ala Glu Asp
210                 215                 220

Thr Ala Val Tyr Tyr Cys Ala Arg Asp Pro Ile Tyr Ala Ser Ser Ser
225                 230                 235                 240

Gly Tyr Ala Asp Ile Trp Gly Gln Gly Thr Leu Val Thr Val Ser Ser
                245                 250                 255

<210> SEQ ID NO 10
<211> LENGTH: 20
<212> TYPE: PRT
<213> ORGANISM: Artificial Sequence
<220> FEATURE:
<223> OTHER INFORMATION: linker

<400> SEQUENCE: 10

Gly Gly Gly Gly Ser Gly Gly Gly Ser Gly Gly Gly Gly Ser Gly
1               5                   10                  15

Gly Gly Gly Ser
            20

<210> SEQ ID NO 11
<211> LENGTH: 247
<212> TYPE: PRT
<213> ORGANISM: Artificial Sequence
<220> FEATURE:
<223> OTHER INFORMATION: DLX105

<400> SEQUENCE: 11

Met Ala Asp Ile Val Met Thr Gln Ser Pro Ser Ser Leu Ser Ala Ser
1               5                   10                  15

Val Gly Asp Arg Val Thr Leu Thr Cys Thr Ala Ser Gln Ser Val Ser
            20                  25                  30

Asn Asp Val Val Trp Tyr Gln Gln Arg Pro Gly Lys Ala Pro Lys Leu
        35                  40                  45

-continued

```
Leu Ile Tyr Ser Ala Phe Asn Arg Tyr Thr Gly Val Pro Ser Arg Phe
    50                  55                  60

Ser Gly Arg Gly Tyr Gly Thr Asp Phe Thr Leu Thr Ile Ser Ser Leu
65                  70                  75                  80

Gln Pro Glu Asp Val Ala Val Tyr Tyr Cys Gln Gln Asp Tyr Asn Ser
            85                  90                  95

Pro Arg Thr Phe Gly Gln Gly Thr Lys Leu Glu Val Lys Arg Gly Gly
            100                 105                 110

Gly Gly Ser Gly Gly Gly Gly Ser Gly Gly Gly Gly Ser Ser Gly Gly
        115                 120                 125

Gly Ser Gln Val Gln Leu Val Gln Ser Gly Ala Glu Val Lys Lys Pro
    130                 135                 140

Gly Ala Ser Val Lys Val Ser Cys Thr Ala Ser Gly Tyr Thr Phe Thr
145                 150                 155                 160

His Tyr Gly Met Asn Trp Val Arg Gln Ala Pro Gly Lys Gly Leu Glu
                165                 170                 175

Trp Met Gly Trp Ile Asn Thr Tyr Thr Gly Glu Pro Thr Tyr Ala Asp
            180                 185                 190

Lys Phe Lys Asp Arg Phe Thr Phe Ser Leu Glu Thr Ser Ala Ser Thr
        195                 200                 205

Val Tyr Met Glu Leu Thr Ser Leu Thr Ser Asp Asp Thr Ala Val Tyr
    210                 215                 220

Tyr Cys Ala Arg Glu Arg Gly Asp Ala Met Asp Tyr Trp Gly Gln Gly
225                 230                 235                 240

Thr Leu Val Thr Val Ser Ser
                245
```

UNITED STATES PATENT AND TRADEMARK OFFICE
CERTIFICATE OF CORRECTION

PATENT NO. : 10,233,238 B2
APPLICATION NO. : 15/127976
DATED : March 19, 2019
INVENTOR(S) : Shamshiev et al.

Page 1 of 1

It is certified that error appears in the above-identified patent and that said Letters Patent is hereby corrected as shown below:

In the Claims

Column 62, Claim 23, Line 5:
Please correct "antibody of fragment" to read -- antibody or fragment --

Signed and Sealed this
Sixteenth Day of July, 2019

Andrei Iancu
*Director of the United States Patent and Trademark Office*